(12) United States Patent
Aoyama et al.

(10) Patent No.: US 8,268,457 B2
(45) Date of Patent: Sep. 18, 2012

(54) ORGANIC ELECTROLUMINESCENT DEVICE AND MATERIAL FOR ORGANIC ELECTROLUMINESCENT DEVICE

(75) Inventors: Yoshiaki Aoyama, Sodegaura (JP); Hironobu Morishita, Sodegaura (JP); Chishio Hosokawa, Sodegaura (JP); Shigeyuki Matsunami, Shinagawa-ku (JP); Yasunori Kijima, Shinagawa-ku (JP)

(73) Assignees: Idemitsu Kosan Co., Ltd., Tokyo (JP); Sony Corporation, Tokyo (JP)

( * ) Notice: Subject to any disclaimer, the term of this patent is extended or adjusted under 35 U.S.C. 154(b) by 811 days.

(21) Appl. No.: 12/314,233

(22) Filed: Dec. 5, 2008

(65) Prior Publication Data

US 2009/0167167 A1    Jul. 2, 2009

Related U.S. Application Data

(63) Continuation of application No. PCT/JP2007/061332, filed on Jun. 5, 2007.

(30) Foreign Application Priority Data

Jun. 5, 2006 (JP) .................. 2006-156445

(51) Int. Cl.
  *H01L 51/54* (2006.01)
  *C07D 471/00* (2006.01)
(52) U.S. Cl. ........ 428/690; 428/917; 313/504; 313/506; 257/E51.05; 544/338; 544/345
(58) Field of Classification Search .................. None
  See application file for complete search history.

(56) References Cited

U.S. PATENT DOCUMENTS

| | | | |
|---|---|---|---|
| 3,112,197 A | 11/1963 | Neugebauer et al. |
| 3,180,703 A | 4/1965 | Ableson et al. |
| 3,180,729 A | 4/1965 | Klupfel et al. |
| 3,180,730 A | 4/1965 | Klupfel et al. |
| 3,189,447 A | 6/1965 | Neugebauer et al. |
| 3,240,597 A | 3/1966 | Fox |
| 3,257,203 A | 6/1966 | Süs et al. |
| 3,476,754 A | 11/1969 | Cain |
| 3,526,501 A | 9/1970 | Fox |
| 3,542,544 A | 11/1970 | Seus et al. |
| 3,542,547 A | 11/1970 | Wilson |
| 3,567,450 A | 3/1971 | Brantly et al. |
| 3,615,402 A | 10/1971 | Rule |
| 3,615,404 A | 10/1971 | Price et al. |
| 3,658,520 A | 4/1972 | Brantly et al. |
| 3,717,462 A | 2/1973 | Negishi et al. |
| 3,820,989 A | 6/1974 | Rule et al. |
| 3,837,851 A | 9/1974 | Shattuck et al. |
| 3,963,779 A | 6/1976 | Tsukahara et al. |
| 4,012,376 A | 3/1977 | Wright |
| 4,123,269 A | 10/1978 | Von Hoene et al. |
| 4,127,412 A | 11/1978 | Rule et al. |
| 4,150,987 A | 4/1979 | Anderson et al. |
| 4,175,961 A | 11/1979 | Wright et al. |
| 4,232,103 A | 11/1980 | Limburg et al. |
| 4,233,384 A | 11/1980 | Turner et al. |
| 4,251,612 A | 2/1981 | Chu et al. |
| 4,273,846 A | 6/1981 | Pai et al. |
| 4,278,746 A | 7/1981 | Goto et al. |
| 4,306,008 A | 12/1981 | Pai et al. |
| 4,588,666 A | 5/1986 | Stolka et al. |
| 4,665,000 A | 5/1987 | Tokoli et al. |
| 4,720,432 A | 1/1988 | VanSlyke et al. |
| 4,950,950 A | 8/1990 | Perry et al. |
| 5,061,569 A | 10/1991 | VanSlyke et al. |
| 2002/0055014 A1 | 5/2002 | Okada et al. |

FOREIGN PATENT DOCUMENTS

| | | |
|---|---|---|
| CA | 917980 | 1/1973 |
| CA | 1104866 | 7/1981 |
| DE | 1110518 | 7/1961 |
| EP | 0 001 599 A1 | 5/1979 |
| EP | 0 029 703 A1 | 6/1981 |
| EP | 0 278 758 A2 | 8/1988 |
| GB | 1 413 352 | 11/1975 |
| GB | 1 505 409 | 3/1978 |
| JP | 37-16096 | 10/1962 |
| JP | 39-27577 | 12/1964 |
| JP | 45-555 | 1/1970 |
| JP | 46-3712 | 1/1971 |
| JP | 47-25336 | 7/1972 |
| JP | 49-35702 | 9/1974 |
| JP | 49-105537 | 10/1974 |
| JP | 51-10105 | 4/1976 |
| JP | 51-10983 | 4/1976 |
| JP | 51-93224 | 8/1976 |

(Continued)

OTHER PUBLICATIONS

Machine translation of JP 2004-323434 (Nov. 2004).*

*Primary Examiner* — Marie R. Yamnitzky
(74) *Attorney, Agent, or Firm* — Oblon, Spivak, McClelland, Maier & Neustadt, L.L.P.

(57) ABSTRACT

Disclosed is a novel compound useful as a constituent of an organic EL device. Also disclosed is a practical organic EL device using this compound. This organic EL device has low driving voltage, long life, and reduced leakage current. Specifically disclosed is a compound characterized by having at least one structure (1) shown below in a molecule. Structure (1)

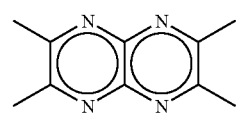

6 Claims, No Drawings

FOREIGN PATENT DOCUMENTS

| | | |
|---|---|---|
| JP | 53-27033 | 3/1978 |
| JP | 54-58445 | 5/1979 |
| JP | 54-59143 | 5/1979 |
| JP | 54-64299 | 5/1979 |
| JP | 54-110536 | 8/1979 |
| JP | 54-110837 | 8/1979 |
| JP | 54-112637 | 9/1979 |
| JP | 54-119925 | 9/1979 |
| JP | 54-149634 | 11/1979 |
| JP | 55-17105 | 2/1980 |
| JP | 55-46760 | 4/1980 |
| JP | 55-51086 | 4/1980 |
| JP | 55-52063 | 4/1980 |
| JP | 55-52064 | 4/1980 |
| JP | 55-74546 | 6/1980 |
| JP | 55-79450 | 6/1980 |
| JP | 55-88064 | 7/1980 |
| JP | 55-88065 | 7/1980 |
| JP | 55-108667 | 8/1980 |
| JP | 55-144250 | 11/1980 |
| JP | 55-156953 | 12/1980 |
| JP | 56-4148 | 1/1981 |
| JP | 56-22437 | 3/1981 |
| JP | 56-36656 | 4/1981 |
| JP | 56-46234 | 4/1981 |
| JP | 56-80051 | 7/1981 |
| JP | 56-88141 | 7/1981 |
| JP | 56-119132 | 9/1981 |
| JP | 57-11350 | 1/1982 |
| JP | 57-45545 | 3/1982 |
| JP | 57-148749 | 9/1982 |
| JP | 60-93455 | 5/1985 |
| JP | 60-94462 | 5/1985 |
| JP | 60-174749 | 9/1985 |
| JP | 60-175052 | 9/1985 |
| JP | 61-14642 | 1/1986 |
| JP | 61-72255 | 4/1986 |
| JP | 61-98353 | 5/1986 |
| JP | 61-210363 | 9/1986 |
| JP | 61-228451 | 10/1986 |
| JP | 61-295558 | 12/1986 |
| JP | 62-10652 | 1/1987 |
| JP | 62-30255 | 2/1987 |
| JP | 62-36674 | 2/1987 |
| JP | 62-47646 | 3/1987 |
| JP | 63-295695 | 12/1988 |
| JP | 1-211399 | 8/1989 |
| JP | 2-204996 | 8/1990 |
| JP | 2-282263 | 11/1990 |
| JP | 2-311591 | 12/1990 |
| JP | 3-232886 | 10/1991 |
| JP | 4-308688 | 10/1992 |
| JP | 8-193191 | 7/1996 |
| JP | 2002-319491 | 10/2002 |
| JP | 2003-40873 | 2/2003 |
| JP | 2003-212875 | 7/2003 |
| JP | 2004-161754 | 6/2004 |
| JP | 3571977 | 7/2004 |
| JP | 2004-323434 | 11/2004 |
| JP | 3614405 | 11/2004 |
| JP | 2006-135145 | 5/2006 |
| JP | 2006-232793 | 9/2006 |
| JP | 2006-294895 | 10/2006 |
| WO | WO 01/49806 A1 | 7/2001 |
| WO | WO 2004/037825 A1 | 5/2004 |

* cited by examiner

ORGANIC ELECTROLUMINESCENT DEVICE AND MATERIAL FOR ORGANIC ELECTROLUMINESCENT DEVICE

TECHNICAL FIELD

The present invention relates to a novel material for organic electroluminescence (EL) devices and an organic EL device comprising the material, and relates to an organic EL device having a low driving voltage, a long lifetime, and a small leakage current.

BACKGROUND ART

The organic electroluminescence (EL) device using an organic material has been considered to be hopeful for use as a solid emitting type full color display device, which is cheap and has a large area and accordingly, there have widely been conducted a variety of investigations for the development of such devices. In general, the EL device comprises an emitting layer and a pair of electrodes sandwiching the emitting layer between them. The emission of light from the EL device is such a phenomenon that, when an electric field is applied between these electrodes, electrons are injected into the emitting layer from the side of the cathode, while holes are likewise injected into the layer from the side of the anode, subsequently the electrons are recombined with the holes within the emitting layer to generate excited states and energies are converted in the form of light to be emitted when the excited states are brought back to the ground states.

Conventional organic EL devices have a high driving voltage, and have a large leakage current as well as low luminance and efficiency of light emission, as compared with inorganic light-emitting diodes. In addition, deterioration in the performances of the organic EL devices is rapid. For these reasons, the organic EL devices have not yet been put to practical use. Although the organic EL devices have been gradually improved in these days (see, for example, Patent Document 1 and Patent Document 2), there are still demands for devices having a lower driving voltage, a longer lifetime, and also a smaller leakage current.

Patent Document 1: Japanese Patent No. 3571977.
Patent Document 2: Japanese Patent No. 3614405.

DISCLOSURE OF THE INVENTION

Problems that the Invention is to Solve

The present invention has been made for solving the above problems, and aims at providing a novel compound which is useful as the constituent of organic EL devices, and at achieving a practically-applicable organic EL device having a low driving voltage, a long lifetime, and a small leakage current by using the compound.

Means for Solving the Problems

The inventors of the present invention have conducted various studies to achieve the foregoing objects, have found that, when a novel compound having a specific structure is used for an organic EL device, the resulting organic EL device requires a reduced driving voltage and shows an extended lifetime and a reduced leakage current, and have thus completed the present invention. More specifically, the present invention provides a compound characterized by having at least one structure (1) in one molecule:

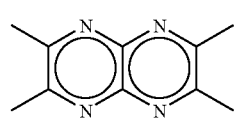

Structure (1)

In addition, the present invention provides a material for organic EL devices, as well as a hole injecting material or a hole transporting material for organic EL devices, the materials comprising the compound according to the present invention.

Moreover, the present invention provides an organic electroluminescence device having at least a pair of electrodes and an organic emitting layer sandwiched by the electrodes, the organic EL device comprising the compound according to the present invention.

Furthermore, the present invention provides an apparatus comprising the organic EL device.

Effects of the Invention

The compound according to the present invention has shown an excellent performance when used as a material for organic EL devices, particularly, as a hole injecting material therefor. Japanese Unexamined Patent Application Publication (hereunder simply referred to as "J.P. KOKAI") No. Hei 03-232886 describes synthesis examples of dicyanotetraazanaphthalenes, but fails to give any specific descriptions as to the properties and application of each compound. In addition, J.P. KOKAI No. 2004-323434 reports that dicyanopyrazinoquinoxaline derivatives are excellent in electron-accepting properties and electron mobility. However, J.P. KOKAI No. 2004-323434 does not describe the performance or the like of an electronic device, for example, an organic EL device, achieved by using the compound in the device, and does not give any example of a case where the compound is used as the material for organic EL devices, particularly, as a hole injecting material therefor, unlike the present invention. Moreover, the compound according to the present invention can achieve optimization of the state of electrons, such as a further enhancement of electron-accepting properties, by combination with an azafluoranthene skeleton in addition to the portion of the structure (1), and also can provide changes in the state of a thin film, such as suppression of crystallization, by changing the three-dimensional structure of the molecule, so that the compound according to the present invention can improve the performance of the organic EL device. Specifically, the compound according to the present invention has high electron-accepting properties, and at the same time, is capable of forming a favorable thin film. Accordingly, the compound according to the present invention makes it possible to achieve an organic EL device that can be driven with a low voltage, has a reduced leakage current, and a longer lifetime, as well as suppressed increase in voltage.

BEST MODE FOR CARRYING OUT THE INVENTION

Compound

A novel compound according to the present invention has at least one structure (1) in one molecule, and favorably two or more structures (1) in one molecule:

Structure (1)

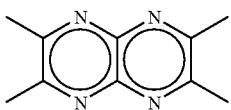

Such compound includes the following compounds, but the present invention is not limited to these.

(1) A compound represented by the following general formula (1):

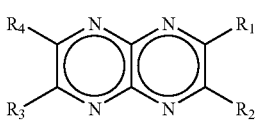

General formula (1)

wherein

R₁ to R₄ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; and those of R₁ to R₄, which are adjacent to one another, may be linked together to form a ring structure.

In the general formula (1), R₁ and R₂ are preferably linked together to form a ring structure. Moreover, it is preferable that R₃ and R₄ be linked together to form a ring structure while R₁ and R₂ are linked together to form a ring structure.

(2) A compound represented by one of the following general formulas (2) to (4):

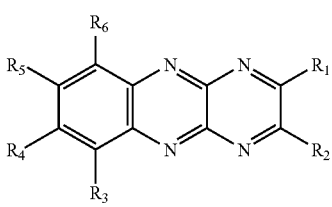

General formula (2)

General formula (3)

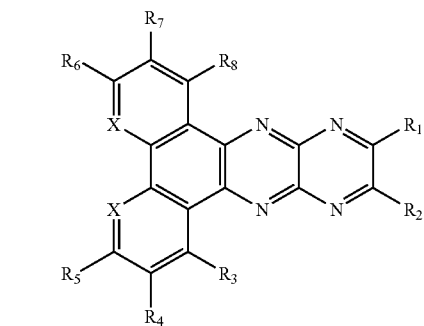

General formula (4)

wherein

R₁ to R₈ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; those of R₁ to R₈, which are adjacent to one another, may be linked together to form a ring structure, provided that at least one of R₃ to R₈ is selected from the group consisting of substituted alkyl groups, substituted aryl groups, substituted or unsubstituted heterocyclic rings, halogen atoms, a cyano group, a nitro group, ester groups, amide groups, substituted or unsubstituted phenoxy groups, and an amino group; and X represents N or CH.

In the general formulas (2) to (4), R₁ and R₂ are preferably a cyano group. Moreover, at least one of R₃ to R₈ is preferably a fluorine-containing substituent.

(3) A compound represented by the following general formula (5):

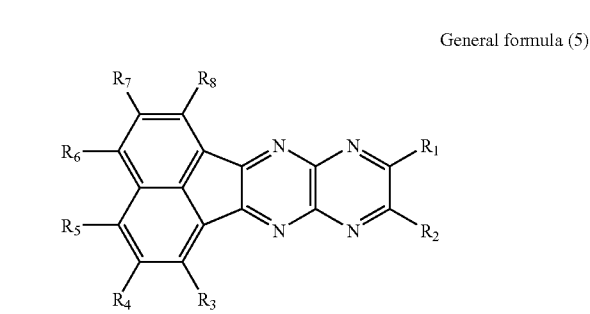

General formula (5)

wherein

R₁ to R₈ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; and those of R₁ to R₈, which are adjacent to one another, may be linked together to form a ring structure.

In the general formula (5), it is preferable that R₁ and R₂ each independently represent an electron withdrawing group selected from the group consisting of halogen atoms, a cyano group, a nitro group, fluoroalkyl groups, and fluoroaryl groups; that R₃ to R₈ be each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy group, substituted or unsubstituted phenoxy groups, and an amino group, and may be the same or different. Those of $R_3$ to $R_8$, which are adjacent to one another, may be linked together to form a ring structure.

In the general formula (5), it is preferable that $R_1$ and $R_2$ are preferably a cyano group. Moreover, at least one of $R_3$ to $R_8$ is preferably a fluorine-containing substituent.

(4) A compound represented by the following general formula (6)

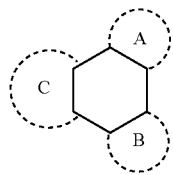

General formula (6)

wherein
the rings A to C each have one of structures (2) to (4), provided that at least one of the rings A to C has the structure (2):

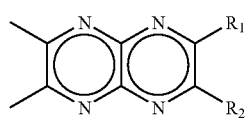

Structure (2)

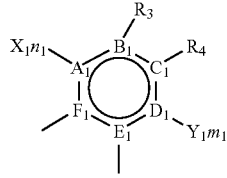

Structure (3)

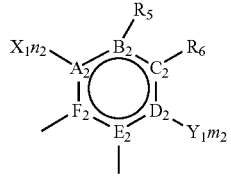

Structure (4)

wherein
$R_1$ to $R_6$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different;

$X_1$ and $X_2$, and $Y_1$ and $Y_2$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different;

those of $R_1$ to $R_6$, $X_1$ and $X_2$, and $Y_1$ and $Y_2$, which are adjacent to one another, may be linked together to form a ring structure;

$n_1$ and $n_2$, and $m_1$ and $m_2$ each represent an integer of 0 or 1; and $A_1, B_1, C_1, D_1, E_1$, and $F_1$ as well as $A_2, B_2, C_2, D_2, E_2$, and $F_2$ form six-membered rings, are each selected from elements belonging to Groups 14 and 15, and may be the same or different.

In the general formula (6), it is preferable that $A_1$ and $A_2$, and $D_1$ and $D_2$ be a nitrogen atom. In addition, it is preferable that $R_1$ and $R_2$ be a cyano group.

(5) A compound represented by the following general formula (7)

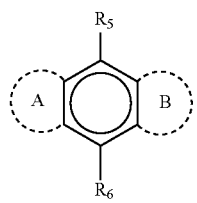

General formula (7)

wherein the rings A and B each have a structure (2) or (3), and at least one of the rings A and B has the structure (2):

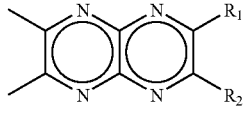

Structure (2)

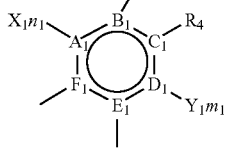

Structure (3)

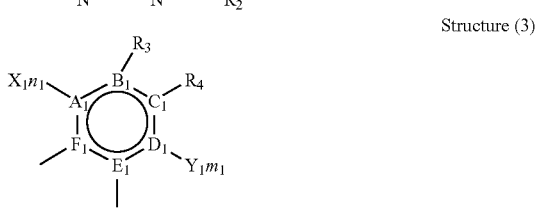

wherein
$R_1$ to $R_6$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different;

$X_1$ and $Y_1$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different;

those of $R_1$ to $R_6$, $X_1$, and $Y_1$, which are adjacent to one another, may be linked together to form a ring structure;

$n_1$ and $m_1$ each represent an integer of 0 or 1;

$A_1, B_1, C_1, D_1, E_1$, and $F_1$ form a six-membered ring, are each selected from the elements belonging to Groups 14 and 15, and may be the same or different.

In the general formula (7), it is preferable that the rings A and B each have the structure (2). In addition, it is preferable that $A_1$ and $D_1$ be a nitrogen atom, and that $R_1$ and $R_2$ be a cyano group.

(6) A compound represented by the following general formula (9) or the following general formula (10):

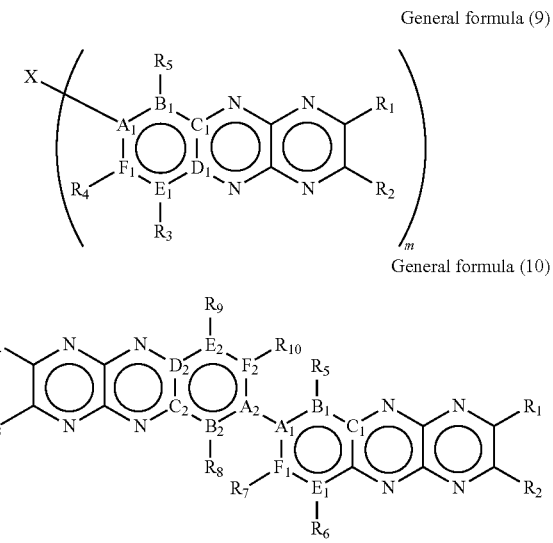

General formula (9)

General formula (10)

wherein $R_1$ to $R_{10}$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different;

X is selected from a group consisting of m-valent groups each derived from substituted or unsubstituted alkanes, substituted or unsubstituted aromatic rings, substituted or unsubstituted heterocyclic rings, substituted or unsubstituted hydroxylated aromatic rings, or amines;

those of $R_1$ to $R_{10}$ and X, which are adjacent to one another, may be linked together to form a ring structure;

m represents an integer of 2 or more; and $A_1$ and $A_2$, $B_1$ and $B_2$, $C_1$ and $C_2$, $D_1$ and $D_2$, $E_1$ and $E_2$, and $F_1$ and $F_2$ form six-membered rings, are each selected from elements belonging to Groups 14 and 15, and may be the same or different.

It is preferable that $R_1$ and $R_2$ in the general formula (9), or $R_1$ to $R_4$ in the general formula (10), be a cyano group. Moreover, it is preferable that $A_1$ and $A_2$, $B_1$ and $B_2$, $C_1$ and $C_2$, $D_1$ and $D_2$, $E_1$ and $E_2$, and $F_1$ and $F_2$ be a carbon atom.

(7) A compound represented by the following general formula (11):

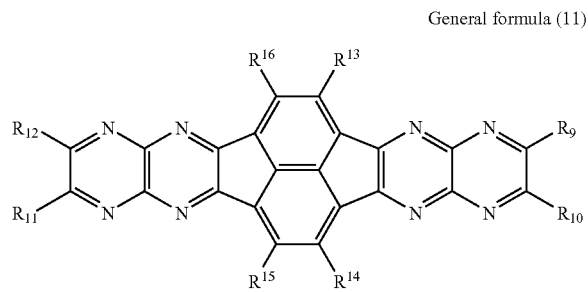

General formula (11)

wherein $R^9$ to $R^{12}$ each independently are an electron withdrawing group selected from the group consisting of halogen atoms, a cyano group, a nitro group, fluoroalkyl groups, and fluoroaryl groups; $R^{13}$ to $R^{16}$ are each independently selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; and those of $R^{13}$ to $R^{16}$, which are adjacent to one another, may be linked together to form a ring structure.

It is preferable that $R^9$ to $R^{12}$ in the general formula (11) be a cyano group.

(8) A compound represented by the following general formula (12):

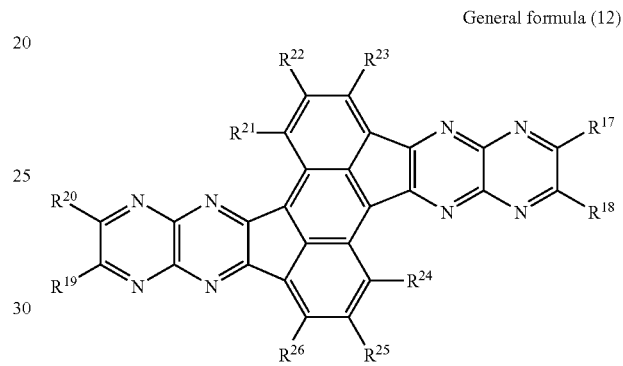

General formula (12)

wherein $R^{17}$ to $R^{20}$ each independently are an electron withdrawing group selected from the group consisting of halogen atoms, a cyano group, a nitro group, fluoroalkyl groups, and fluoroaryl groups; $R^{21}$ to $R^{26}$ are each independently selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; and those of $R^{21}$ to $R^{26}$, which are adjacent to one another, may be linked together to form a ring structure.

It is preferable that $R^{17}$ to $R^{20}$ in the general formula (12) be a cyano group.

In respect of the compounds represented by the foregoing general formulas (1) to (10), the substituted or unsubstituted alkyl groups included in the definition of $R_1$ to $R_4$ appearing in the general formula (1), $R_1$ to $R_5$ appearing in the general formulas (2) to (4), $R_1$ to $R_8$ appearing in the general formula (5), $R_1$ to $R_6$ appearing in the general formula (6), $R_1$ to $R_{16}$ appearing in the general formula (7), $R_1$ to $R_{10}$ appearing in the general formulas (9) and (10), $R^{13}$ to $R^{16}$ appearing in the general formula (11), and $R^{21}$ to $R^{26}$ appearing in the general formula (12), may be a linear or branched one, and preferably has 1 to 30 carbon atoms. In this respect, the substituent thereof includes hydroxyl, amino, cyano, nitro groups; and halogen atoms. The foregoing alkyl groups may have one or a plurality of the foregoing substituents. Specific examples of the alkyl groups include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl groups; cyclic alkyl groups such as cyclohexyl and cyclopentyl groups; fluoroalkyl groups (preferably having 1 to 16 carbon atoms such as trifluoromethyl, pentafluoroethyl, heptafluoropropyl, perfluorocyclohexyl, and perfluoroadamantyl groups); substituted or unsubstituted halogenated alkyl groups having 1 to 30 carbon atoms such as chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, and 1,2,3-triiodopropyl groups; aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, and 1,2,3-trinitropropyl groups. Among them, preferably used herein are substituted or unsubstituted alkyl groups each having 1 to 10 carbon atoms such as methyl, trifluoromethyl, isopropyl, t-butyl, ethyl, propyl, pentafluoroethyl, and cyanomethyl groups.

In respect of the foregoing compounds represented by the foregoing general formulas (1) to (10), the substituted and unsubstituted aryl groups included in the definition of $R_1$ to $R_4$ appearing in the general formula (1), $R_1$ to $R_8$ appearing in the general formulas (2) to (4), $R_1$ to $R_8$ appearing in the general formula (5), $R_1$ to $R_6$ appearing in the general formula (6), $R_1$ to $R_6$ appearing in the general formula (7), $R_1$ to $R_{10}$ appearing in the general formulas (9) and (10), $R^{13}$ to $R^{16}$ appearing in the general formula (11), and $R^{21}$ to $R^{26}$ appearing in the general formula (12), may be monocyclic or polycyclic, and preferably have 6 to 40 atoms forming a ring. Moreover, the substituent thereof includes: alkyl groups having 1 to 20 carbon atoms; alkoxyl groups having 1 to 20 carbon atoms; phenoxy, hydroxy, amino, cyano, and nitro groups; and halogen atoms. The foregoing aryl groups may have one or a plurality of the foregoing substituents. The foregoing aryl groups include fluoroaryl groups (preferably having 6 to 40 of the number of atoms forming a ring such as pentafluorophenyl, tetrafluorophenyl, trifluorophenyl, difluorophenyl, fluorophenyl, trifluoromethylphenyl, bistrifluoromethylphenyl, tristrifluoromethylphenyl, tetratrifluoromethylphenyl, and pentatrifluoromethylphenyl groups). Specific examples of the aryl groups include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, and fluorenyl groups. Among these aryl groups, preferably used herein are substituted or unsubstituted aryl groups having 6 to 20 ring atoms such as phenyl, naphthyl, biphenylyl, anthranyl, phenanthryl, pyrenyl, chrysenyl, fluoranthenyl and fluorenyl groups. These groups may have the substituents specified above.

In respect of the foregoing compounds represented by the foregoing general formulas (1) to (10), the substituted and unsubstituted heterocyclic rings included in the definition of $R_1$ to $R_4$ appearing in the general formula (1), $R_1$ to $R_5$ appearing in the general formulas (2) to (4), $R_1$ to $R_5$ appearing in the general formula (5), $R_1$ to $R_6$ appearing in the general formula (6), $R_1$ to $R_6$ appearing in the general formula (7), $R_1$ to $R_{10}$ appearing in the general formulas (9) and (10), $R^{13}$ to $R^{16}$ appearing in the general formula (11), and $R^{21}$ to $R^{26}$ appearing in the general formula (12), may be monocyclic or polycyclic, and preferably have 3 to 18 ring atoms. Moreover, the substituent thereof includes: alkyl groups having 1 to 20 carbon atoms; alkoxyl groups having 1 to 20 carbon atoms; phenoxy, hydroxy, amino, cyano, and nitro groups; and halogen atoms. The foregoing aryl group may have one or a plurality of the foregoing substituents. Specific examples of the heterocyclic rings include 1-pyrrolidyl, 2-pyrrolidyl, 3-pyrrolidyl, 1-piperidyl, 2-piperidyl, 3-piperidyl, 4-piperidyl, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline, 6-yl, 1,9-phenanthroline-7-yl, 1,9-phenanthrohne-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, and 4-t-butyl-3-indolyl groups. Among these heterocyclic rings, preferably used herein are substituted or unsubstituted heterocyclic rings having 5 to 20 ring atoms such as pyridyl, pyrazyl, quinolyl, quinoxalyl, and phenanthrolinyl groups.

In respect of the foregoing compounds represented by the foregoing general formulas (1) to (10), groups, other than the foregoing groups, included in the definition of $R_1$ to $R_4$ appearing in the general formula (1), $R_1$ to $R_8$ appearing in the general formulas (2) to (4), $R_1$ to $R_8$ appearing in the general formula (5), $R_1$ to $R_6$ appearing in the general formula (6), $R_1$ to $R_6$ appearing in the general formula (7), $R_1$ to $R_{10}$ appearing in the general formulas (9) and (10), $R^9$ to $R^{16}$ appearing in the general formula (11), and $R^{17}$ to $R^{26}$ appearing in the general formula (12), may be, for instance, those listed below:

The halogen atom includes fluorine, chlorine, bromine, and iodine atoms;

The ester group preferably includes one having 1 to 6 carbon atoms for example methoxycarbonyl, ethoxycarbonyl, propoxycarbonyl, and isopropoxycarbonyl groups;

The amide groups include a carboxamide group (—(C═O)NH$_2$), an N-methylcarboxamide group (—(C═O)NMe$_2$), and an N-phenyl-N-methylcarboxamide group (—(C═O)NPh$_2$);

The alkoxy groups and the substituted or unsubstituted phenoxy groups each are a group represented by —OY, wherein Y and the substituents of the phenoxy group include those listed above in connection with the foregoing alkyl and aryl groups, and preferably are substituted or unsubstituted phenoxy groups having 1 to 30 carbon atoms; and Other groups include cyano, nitro, and amino groups.

In respect to the foregoing compounds represented by the foregoing general formulas (6) to (10), the substituted or unsubstituted alkyl groups, the substituted or unsubstituted aryl groups, the substituted or unsubstituted heterocyclic rings, the halogen atoms, the cyano group, the nitro group, the ester groups, the amide groups, the alkoxy groups, the substituted or unsubstituted phenoxy groups, and the amino group represented by $X_1$ and $X_2$, and $Y_1$ and $Y_2$ appearing in the general formula (6), $X_1$ and $Y_1$ appearing in the general formula (7), and X appearing in the general formulas (9) and (10) are the same as those listed above.

Note that, in respect to the foregoing compounds represented by the foregoing general formulas (6) to (10), those of $R_1$ to $R_6$, $X_1$ and $X_2$, and $Y_1$ and $Y_2$, which are adjacent to one another, appearing in the general formula (6), those of $R_1$ to $R_4$, $X_1$, and $Y_1$, which are adjacent to one another, appearing in the general formula (7), and those of $R_1$ to $R_{10}$, and X, which are adjacent to one another, appearing in the general formulas (9) and (10), may be linked together to form a ring structure, and preferably are linked together to form an aromatic ring, more preferably a five-membered aromatic ring or a six-membered aromatic ring, and particularly preferably a six-membered aromatic ring.

In respect to the foregoing compounds represented by the foregoing general formulas (6) to (10), $A_1$, $B_1$, $C_1$, $D_1$, $E_1$, and $F_1$ as well as $A_2$, $B_2$, $C_2$, $D_2$, $E_2$, and $F_2$ appearing in the general formula (6), $A_1$, $B_1$, $C_1$, $D_1$, $E_1$ and $F_1$ appearing in the general formula (7), and $A_1$, $B_1$, $C_1$, $D_1$, $E_1$, and $F_1$ as well as $A_2$, $B_2$, $C_2$, $D_2$, $E_2$, and $F_2$ appearing in the general formulas (9) and (10) form a six-membered ring, are each selected from elements belonging to Group 14 and 15, and may be the same or different. The elements belonging to Group 14 and 15 include C, N, Si, and P. Among these elements, C or N is preferable.

Specific examples of the compounds represented by the foregoing general formulas (1) to (10) are shown below:

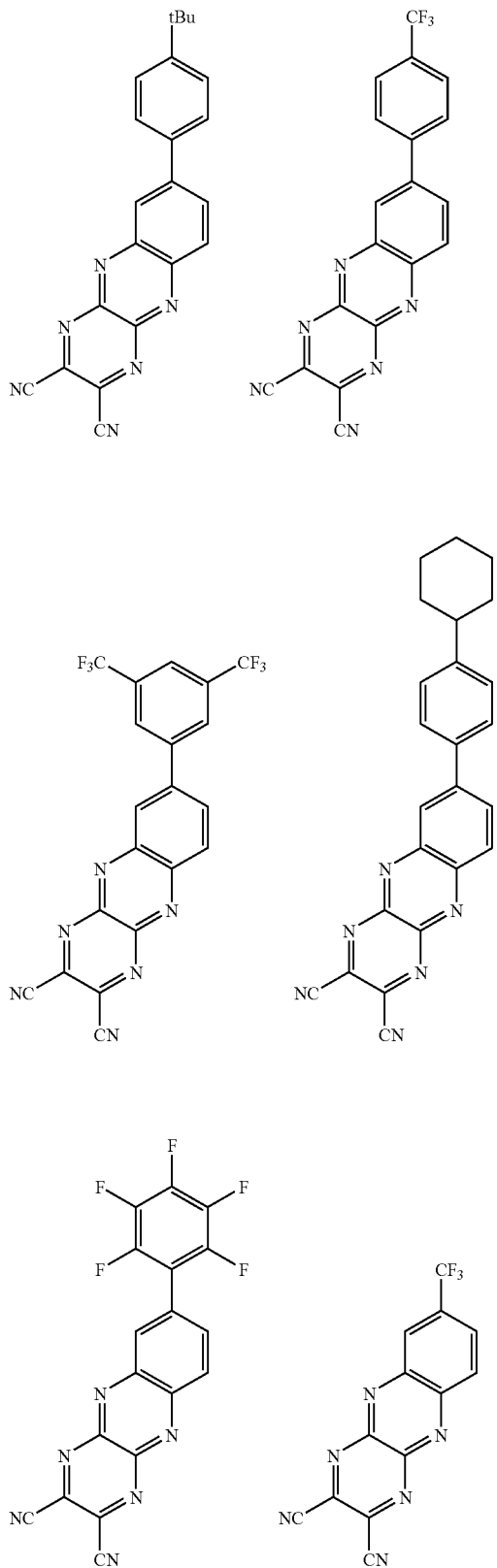

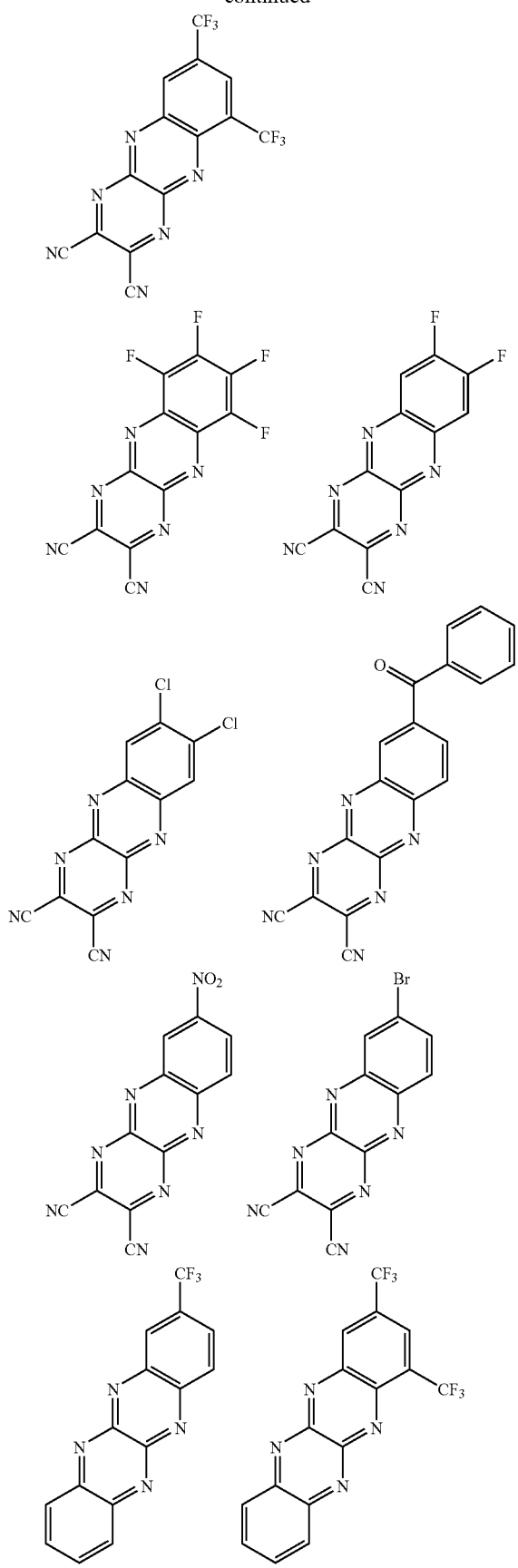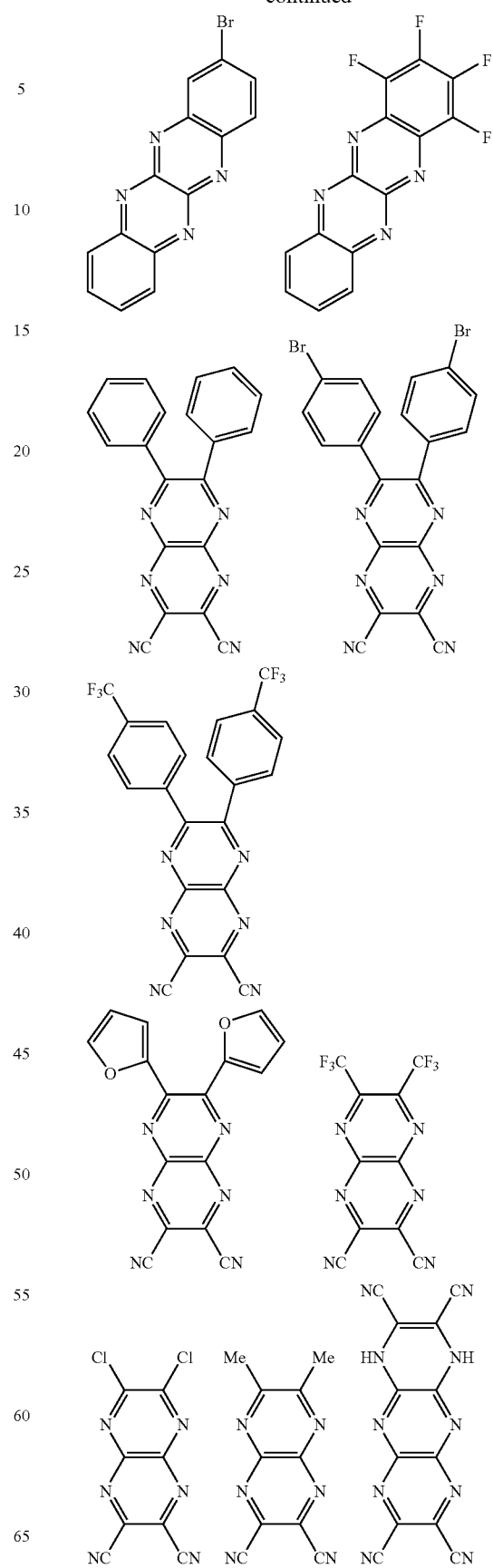

15 -continued
16 -continued
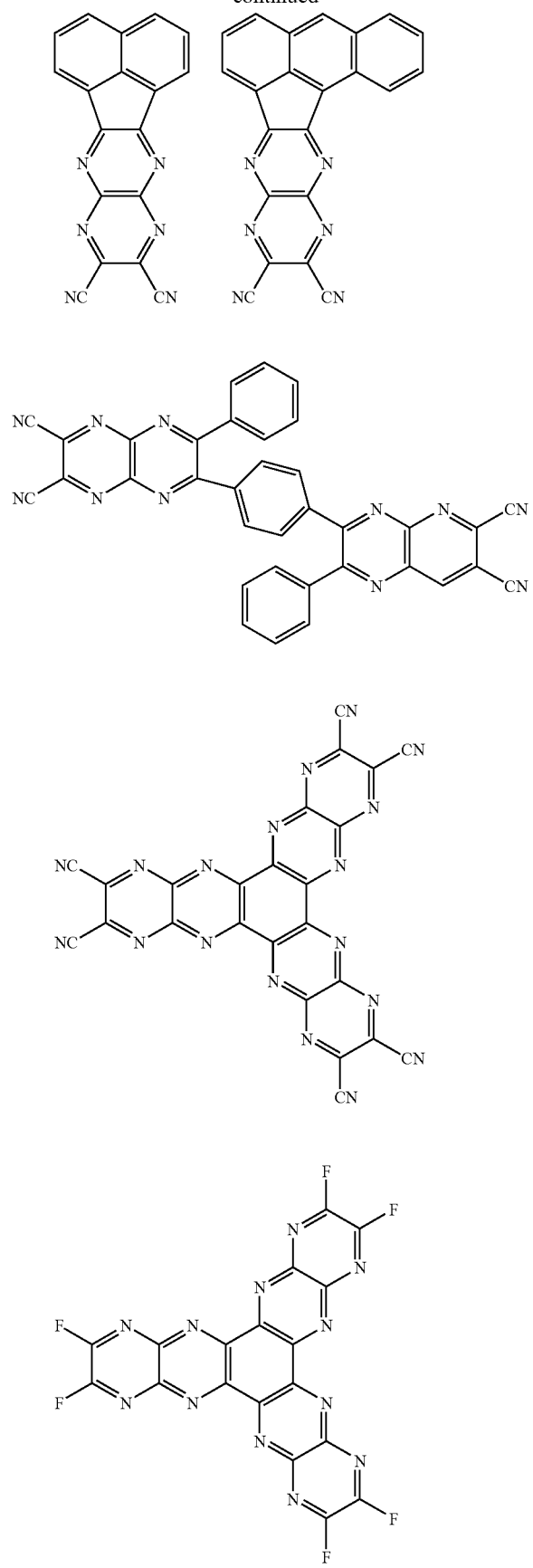
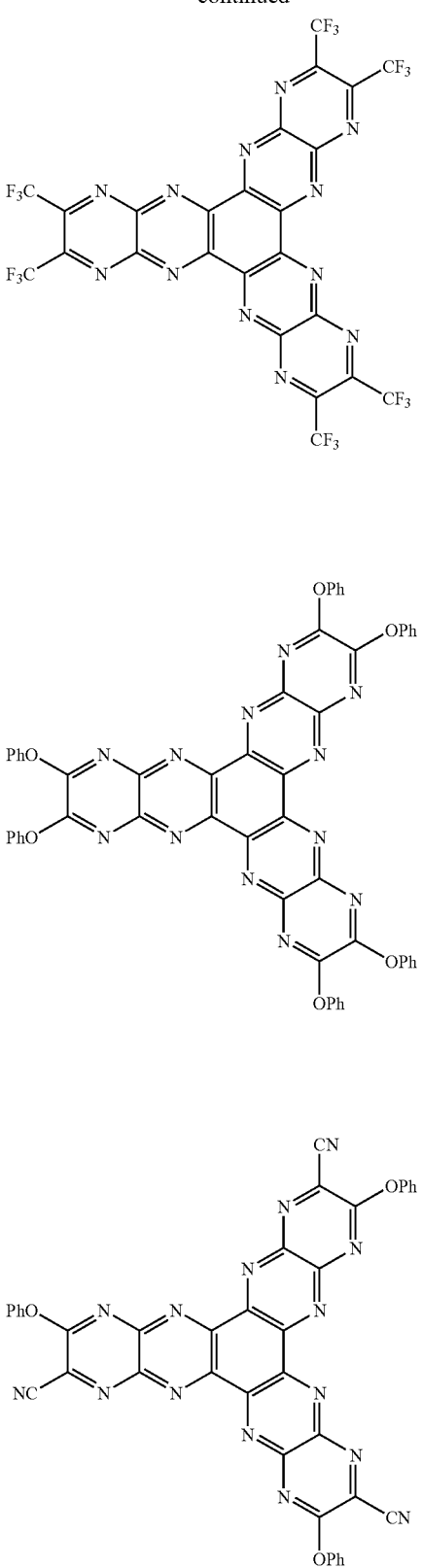

-continued
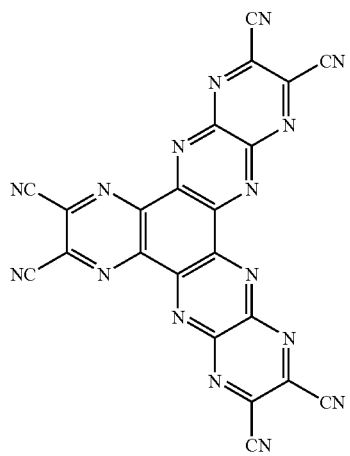
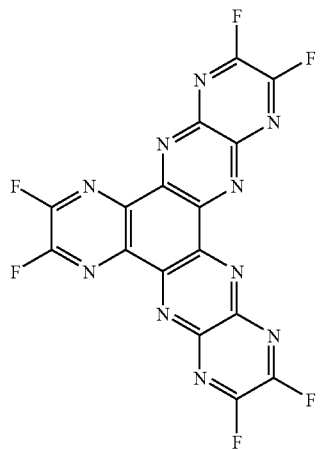
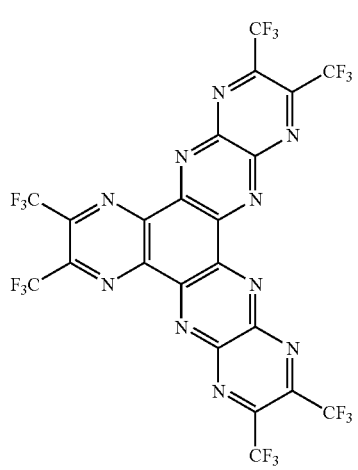
-continued
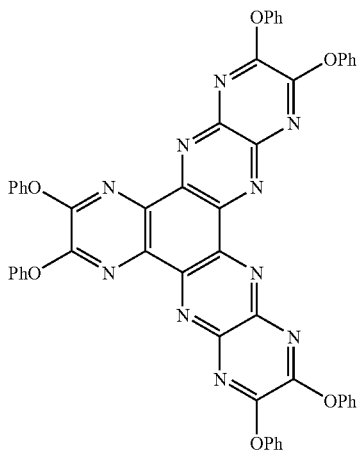
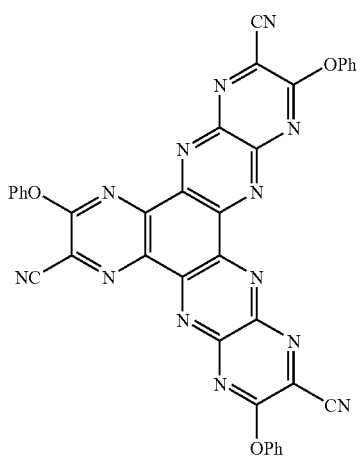
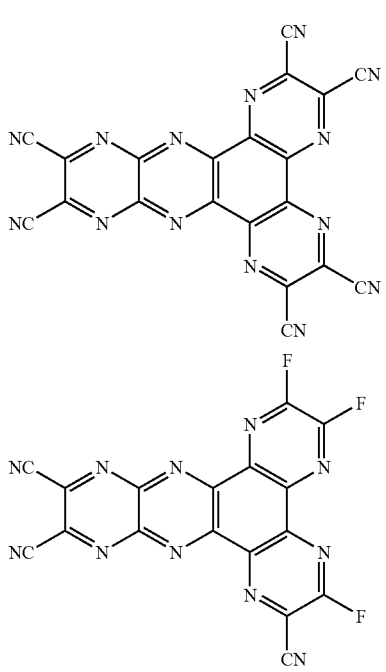

-continued
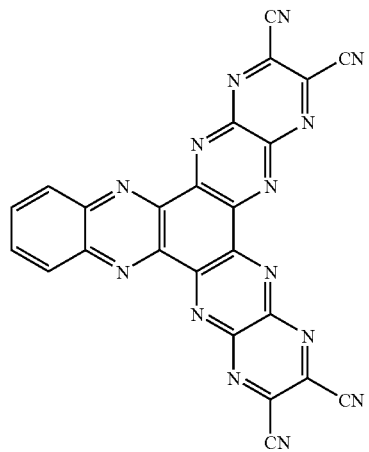
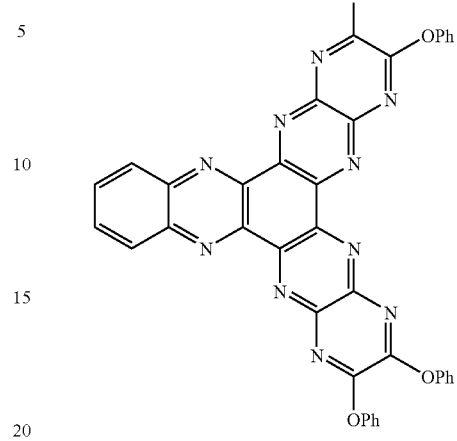
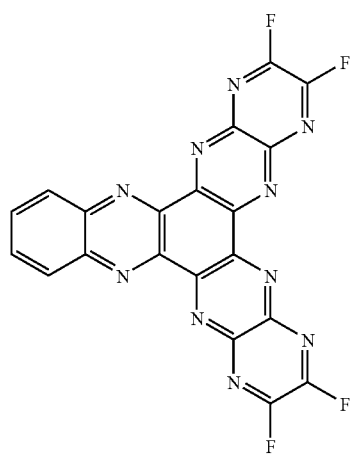
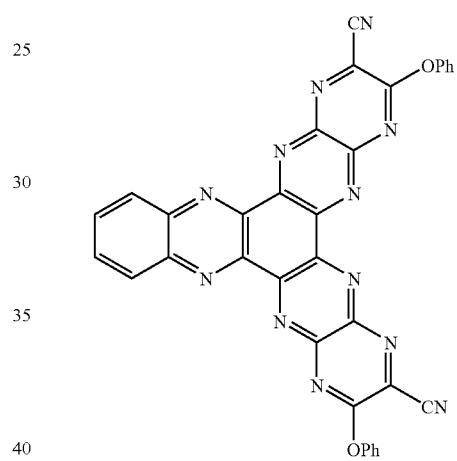
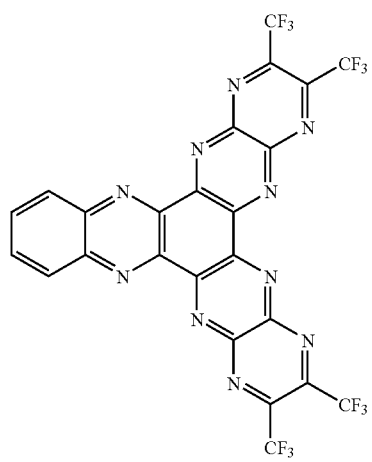
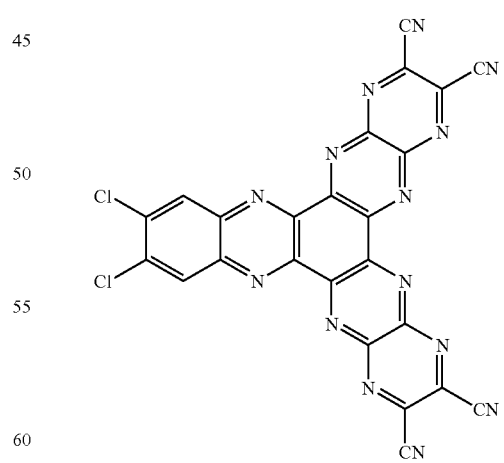

-continued
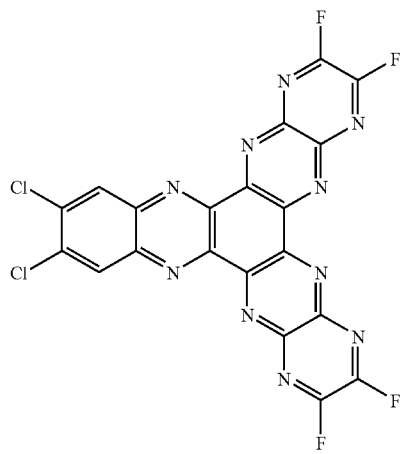
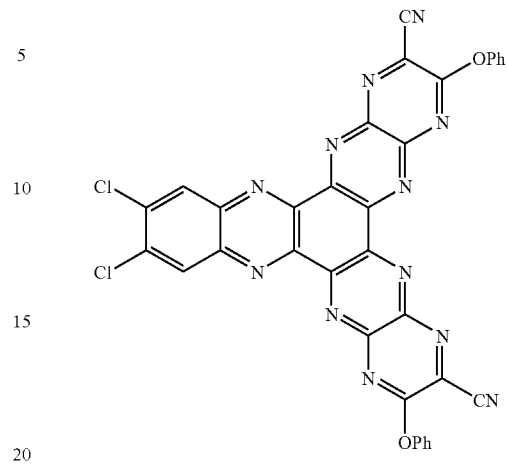
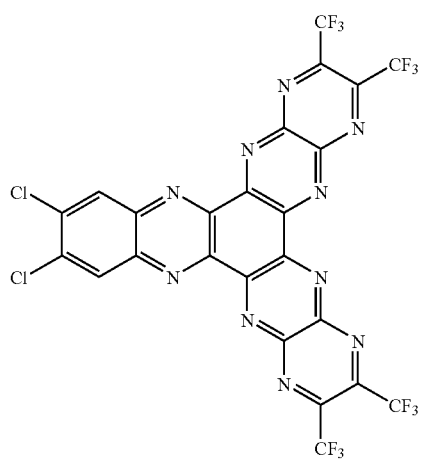
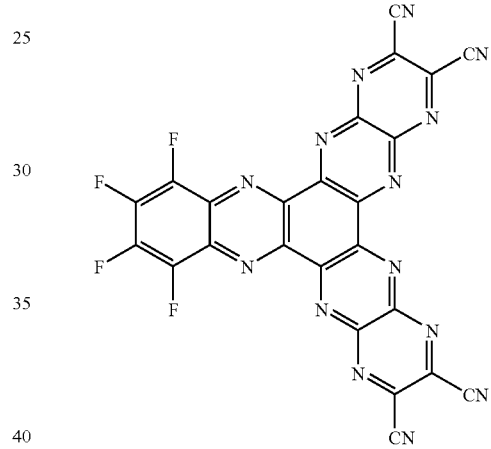
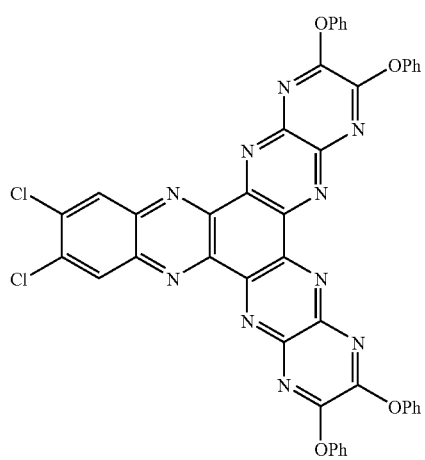
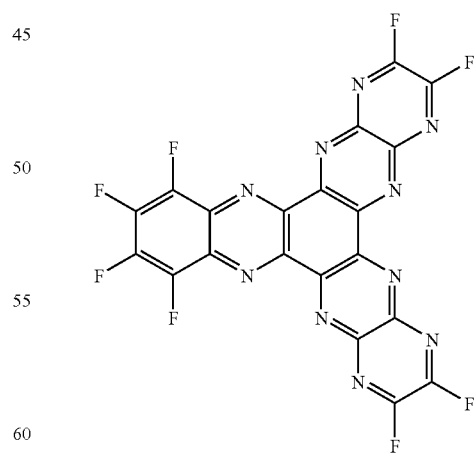

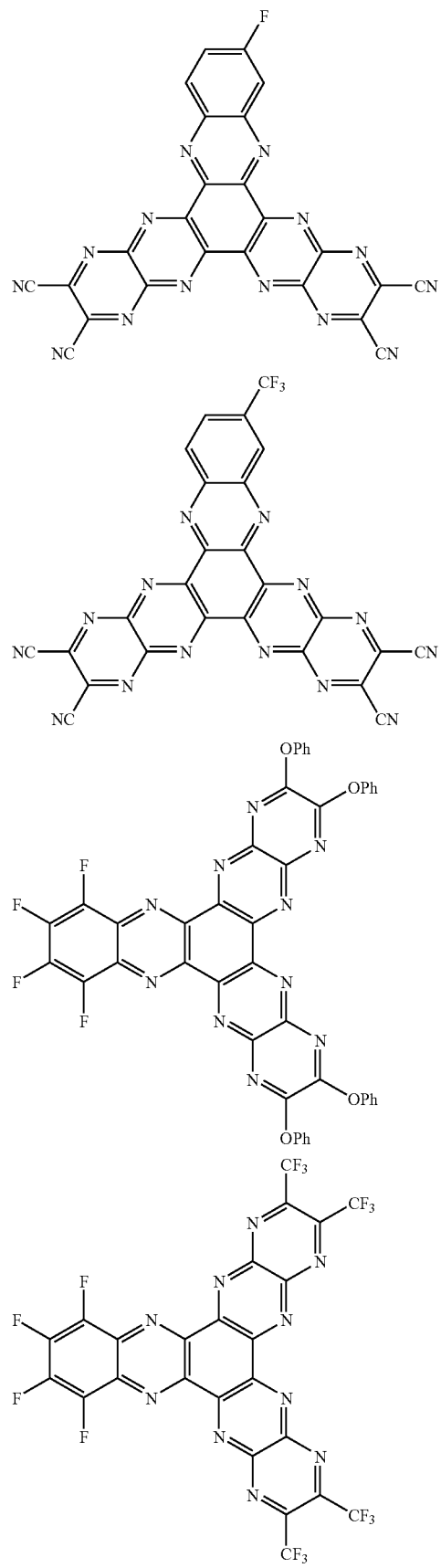
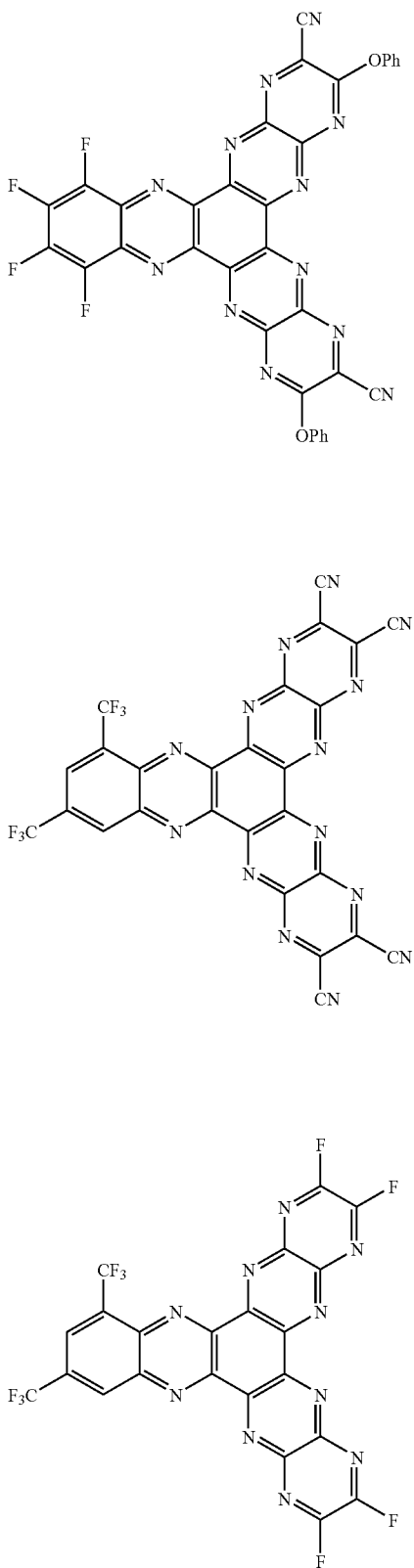

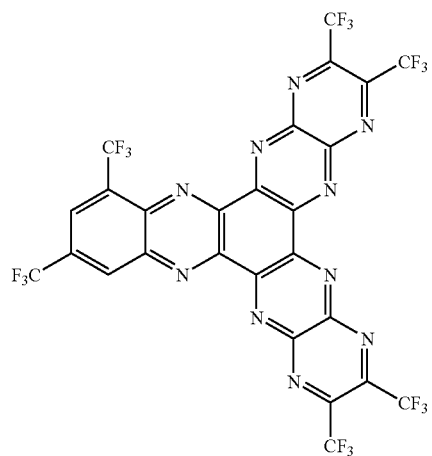
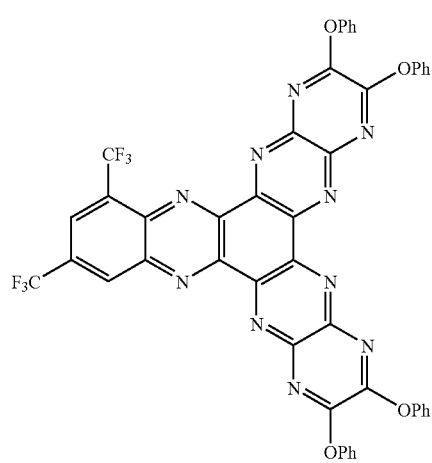
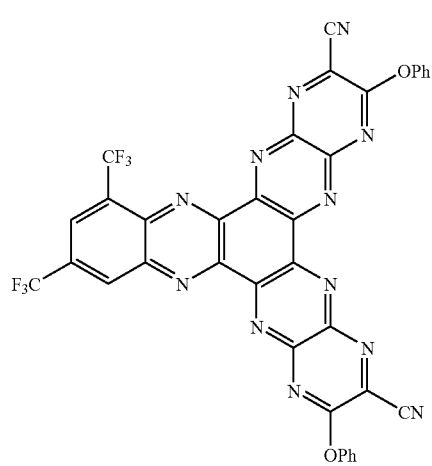
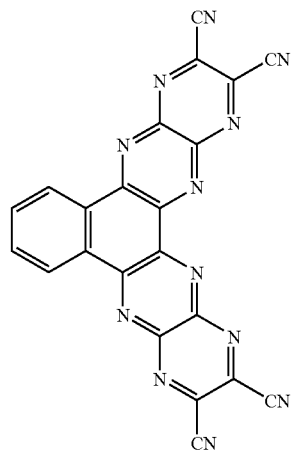
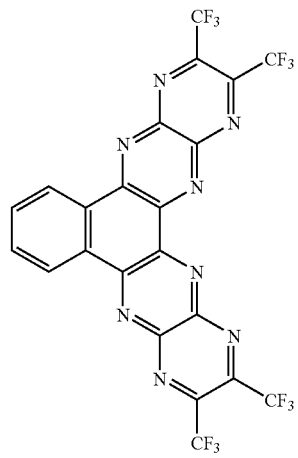

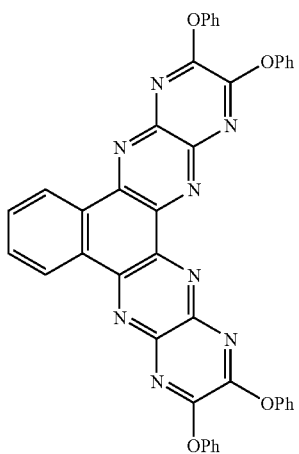
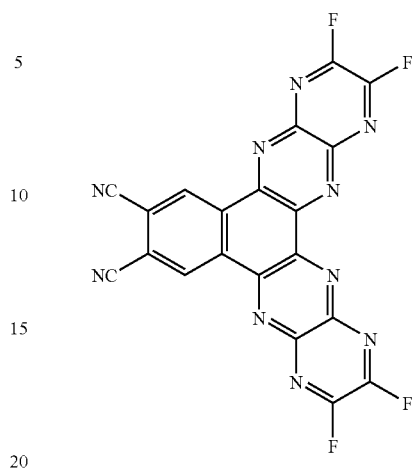
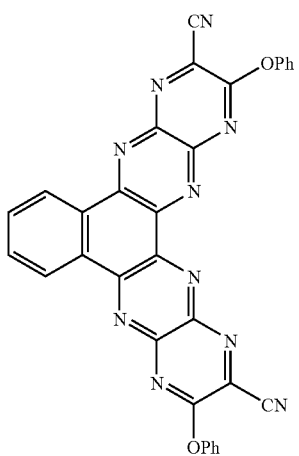
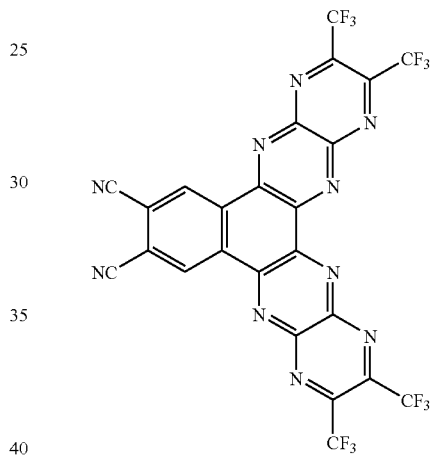
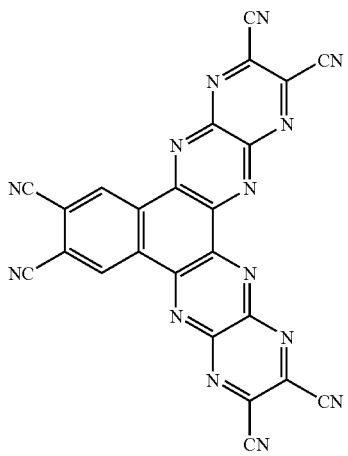
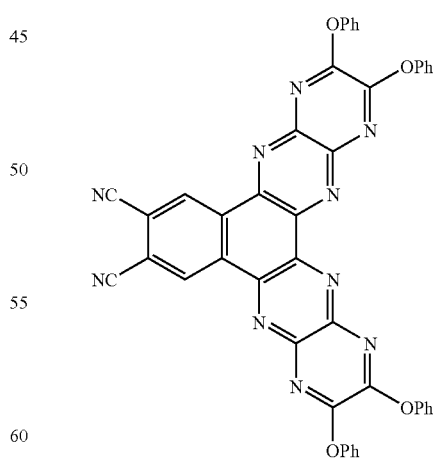

-continued
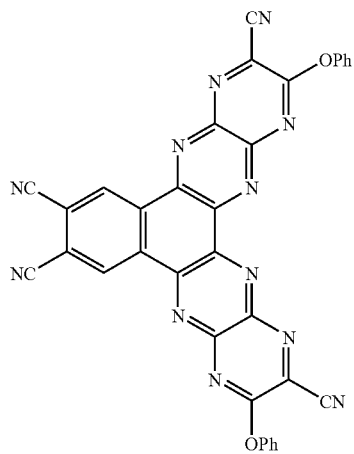
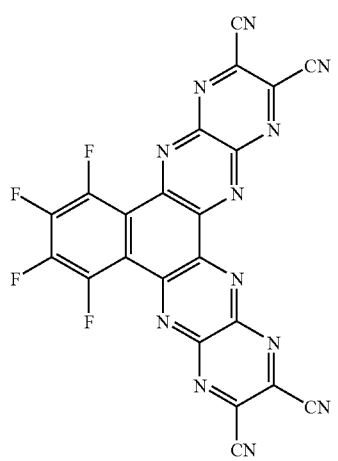
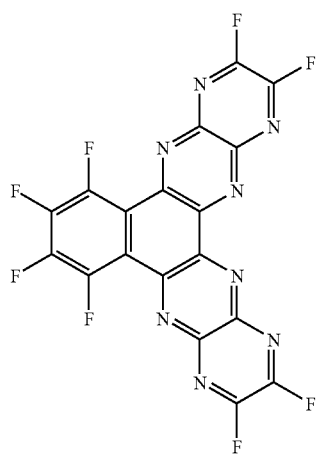
-continued
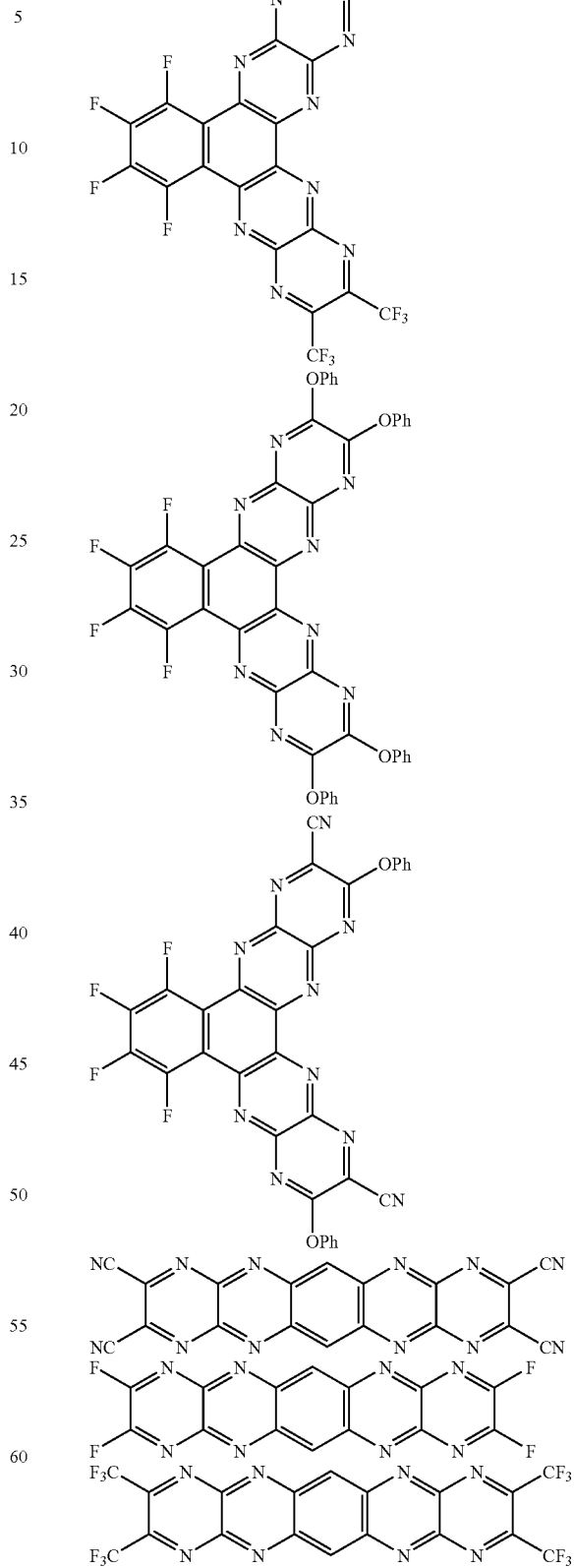

-continued
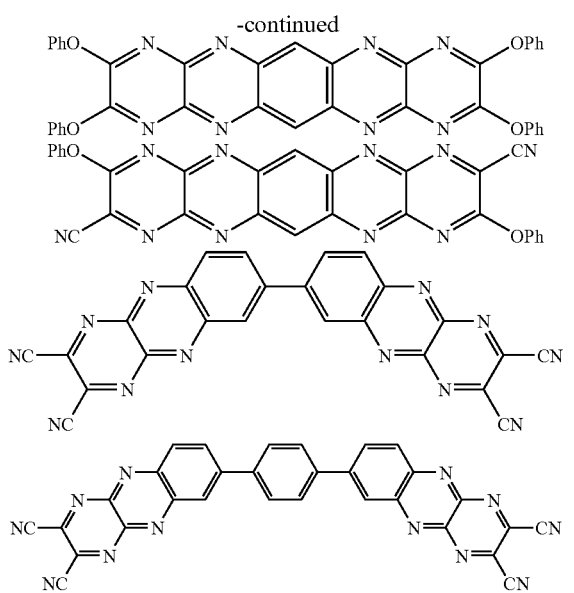
-continued
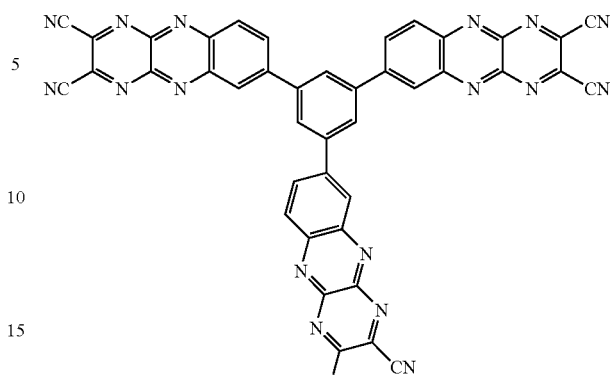
In addition, specific examples of the compounds represented by the general formulas (5), (11), and (12) are shown below:
(A-1)
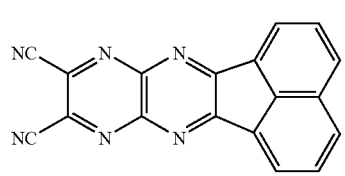
(A-2)
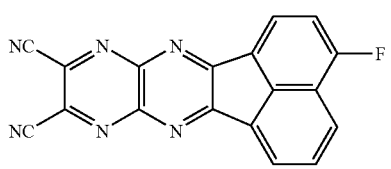
(A-3)
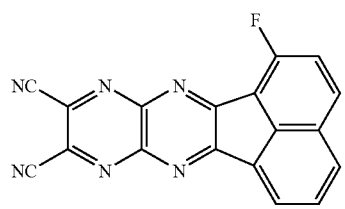
(A-4)
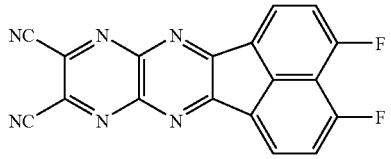
(A-5)
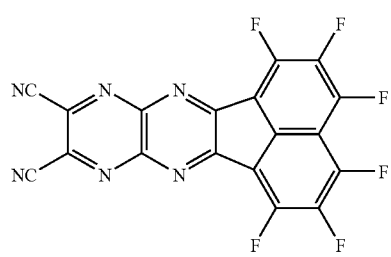
(A-6)
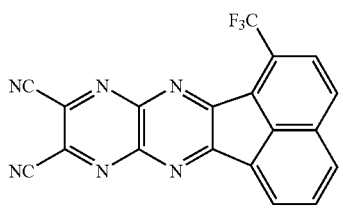
(A-7)
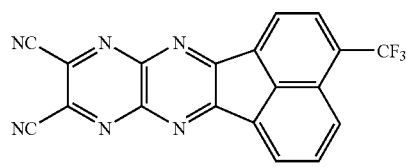
(A-8)
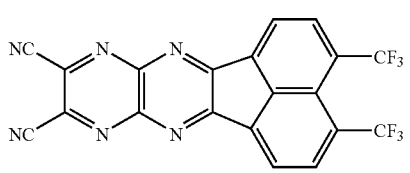
(A-9)
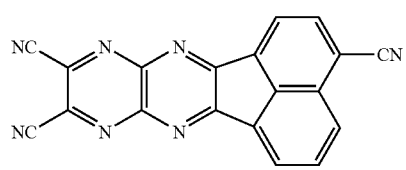
(A-10)
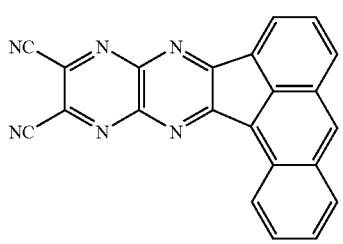

-continued
(A-11) 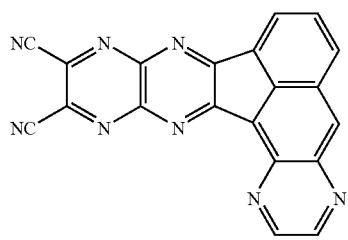
(A-12) 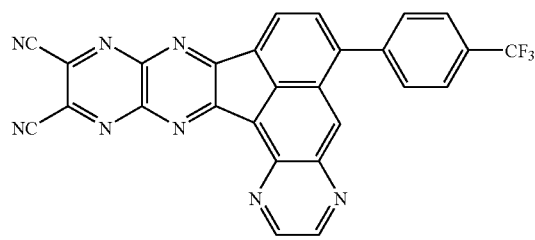
(A-13) 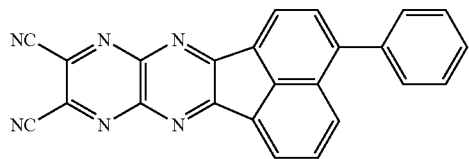
(A-14) 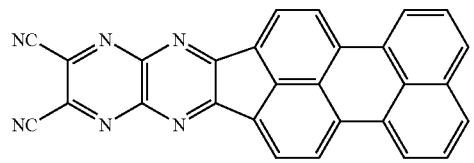
(A-15) 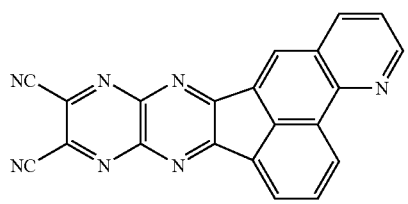
(A-16) 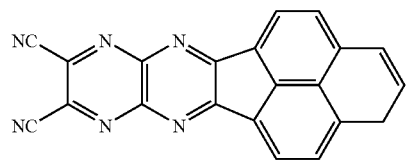
(A-17) 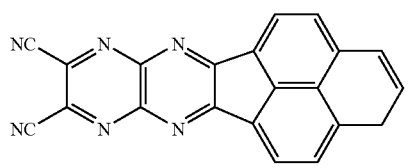
(A-18) 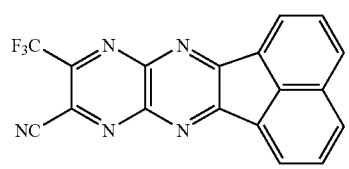
(A-19) 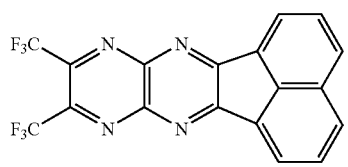
(A-20) 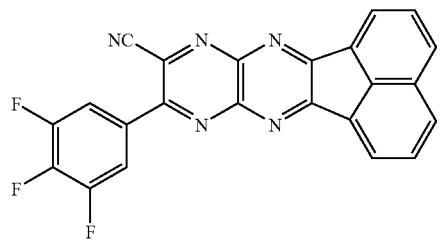
(A-21) 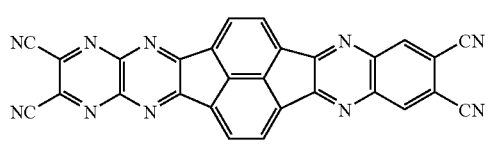
(A-22) 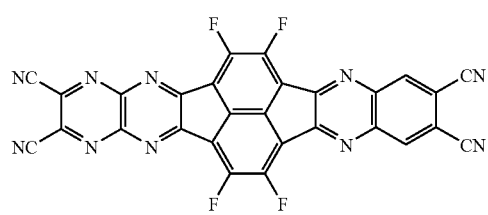
(A-23) 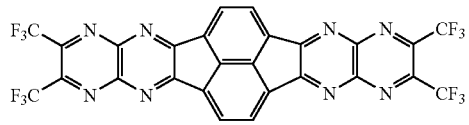
(A-24) 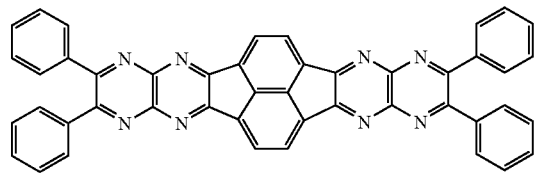

-continued

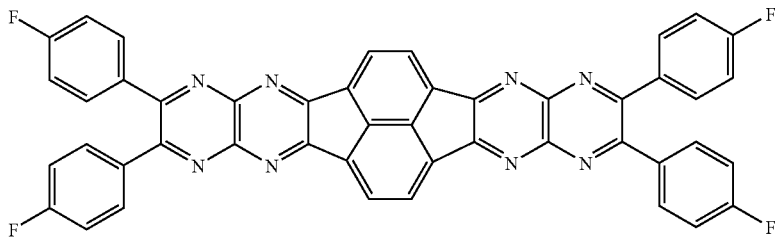

(A-25)

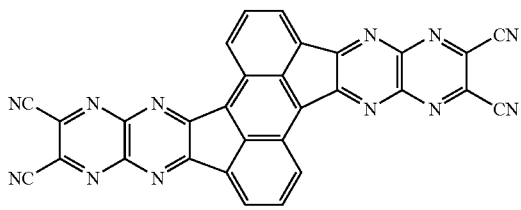

(A-26)

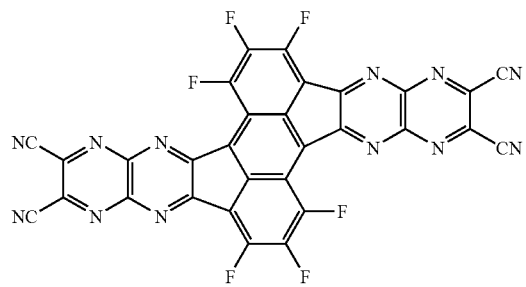

(A-27)

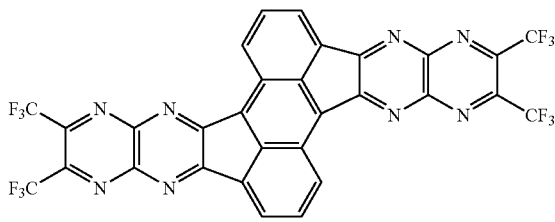

(A-28)

(Method for Synthesizing the Compounds According to the Present Invention)

As an example, here are some of schemes for synthesizing the compounds according to the present invention, but the schemes are not limited to those shown below.

(1) Synthesis method using dichloropyrazine derivatives and amine compounds (refer to Organic Letters Vol. 6, No. 12, 2007 to 2010 (2004), etc.)

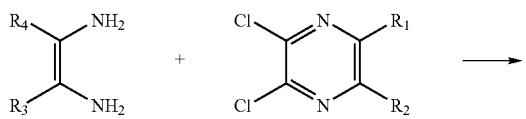

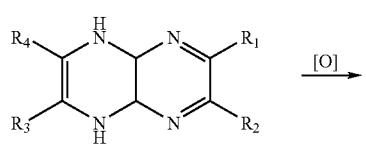

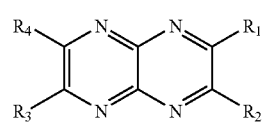

(2) Synthesis method using diaminopyrazine derivatives and carbonyl compounds (refer to Organic Letters Vol. 6, No. 12, 2007 to 2010 (2004), etc.)

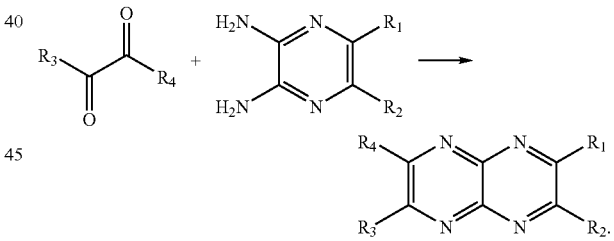

(3) Synthesis method using carbonyl derivatives and amine compounds (refer to Journal of Heterocyclic Chemistry Vol. 34, No. 2, 653 to 657 (1997), etc)

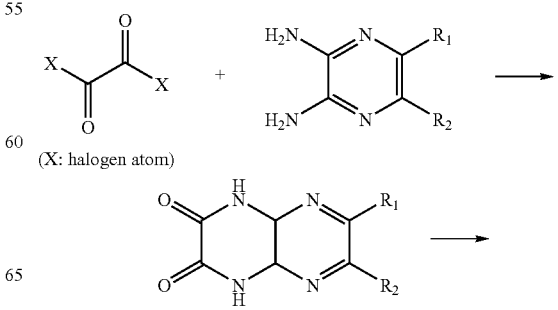

(X: halogen atom)

-continued

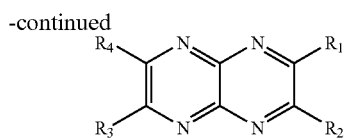

(Constructions of Organic EL device)

The organic EL device according to the present invention is an organic electroluminescence device which comprises at least a pair of electrodes and an organic emitting layer sandwiched by the electrodes, and comprises the compound according to the present invention.

Representative constructions of the organic EL device according to the present invention include:
(1) Anode/emitting layer/cathode;
(2) Anode/hole injection layer/emitting layer/cathode;
(3) Anode/emitting layer/electron injection layer/cathode;
(4) Anode/hole injection layer/emitting layer/electron injection layer/cathode;
(5) Anode/organic semiconductor layer/emitting layer/cathode;
(6) Anode/organic semiconductor layer/electron blocking layer/emitting layer/cathode;
(7) Anode/organic semiconductor layer/emitting layer/adhesion improving layer/cathode;
(8) Anode/hole injection layer/hole transporting layer/emitting layer/electron injection layer/cathode;
(9) Anode/insulating layer/emitting layer/insulating layer/cathode;
(10) Anode/inorganic semiconductor layer/insulating layer/emitting layer/insulating layer/cathode;
(11) Anode/organic semiconductor layer/insulating layer/emitting layer/insulating layer/cathode;
(12) Anode/insulating layer/hole injection layer/hole transporting layer/emitting layer/insulating layer/cathode;
(13) Anode/insulating layer/hole injection layer/hole transporting layer/emitting layer/electron injection layer/cathode.

Among these constructions, those having the construction (8) are preferably used, but the present invention is not limited to these.

The novel compound according to the present invention may be used for any organic thin film layer in an organic EL device, but preferably used for a hole injection layer or a hole transporting layer. Using the novel compound according to the present invention for the hole injection layer or the hole transporting layer makes it possible to achieve a practically-applicable organic EL device having a low driving voltage, a long lifetime, and a small leakage current.

The amount of the novel compound according to the present invention to be contained in the organic thin film layer preferably ranges from 1 to 100 mol %.

(Light-Transmissive Substrate)

The organic EL device according to the present invention is formed on a light-transmissive substrate. The light-transmissive substrate referred to herein is a substrate for supporting the organic EL device, and preferably has a smooth surface and has 50% or more of the light transmittance for the visible range of 400 to 700 nm.

Specific examples of the above substrate include a glass plate and a polymer plate. The above glass substrate include, in particular, soda-lime glass, barium/strontium-containing glass, lead glass, aluminosilicate glass, borosilicate glass, barium-borosilicate glass, and quartz. On the other hand, the above polymer plate include polycarbonate, acrylic resins, polyethylene terephthalate, polyether sulfide, and polysulfone.

(Anode)

The anode of the organic thin-film EL device serves to inject holes into the hole transporting layer or the emitting layer. When the anode side requires transparency, examples of the anode materials used herein include indium tin oxide alloy (ITO), tin oxide (NESA), indium zinc oxide alloy (IZO), gold, silver, platinum, and copper. On the other hand, when the anode is formed as a reflective electrode, which does not require transparency, examples of the anode materials used herein, in addition to the aforementioned metals, include: metals such as aluminum, molybdenum, chromium, and nickel; and alloys thereof.

Although these above materials may be used solely, alloys of these materials, or materials obtained by adding other elements to these materials may be appropriately selected for use.

The anode may be produced by forming a thin film of the foregoing electrode material according to any method such as the vacuum evaporation method or the sputtering method.

In the case where the light emitted from the emitting layer is taken out through the anode, the anode preferably has over 10% of the transmittance for the light emitted from the emitting layer. In addition, the anode preferably has not more than several hundred ($\Omega/\square$) of the sheet resistance. The thickness of the anode may vary depending on the material selected, but generally 10 nm to 1 µm, and preferably 10 to 200 nm.

(Emitting Layer)

The emitting layer of the organic EL device is one having the following functions (1) to (3) in combination:
(1) Injection Function: This function permits the injection of holes through the anode or the hole injection layer and the injection of electrons through the cathode or the electron injection layer upon the application of an electric field to the organic EL device;
(2) Transporting Function: This function permits the transfer of the injected charges (electrons and holes) by the action of the electric field applied to the device;
(3) Emitting Function: This function permits the provision of a field for the recombination of electrons with holes to thus induce the emission of light.

However, although the emitting layer may have a difference between the hole injectability and the electron injectability, or a difference between the transport capacities represented by the hole mobility and electron mobility respectively, it is preferred to move either one of the hole and electron.

This emitting layer can be prepared by any known method such as the vacuum evaporation method, the spin coating method, and the LB method. The emitting layer is particularly preferably a molecular deposit film. In this respect, the terms "molecular deposit film" used herein means a thin film formed by the deposition of a raw compound in a gaseous state; or a film formed through the solidification of a raw compound in a solution or liquid state and thus can in general be distinguished from the thin film (molecular accumulation film) formed using the LB method, on the basis of the differences in the aggregation structure and in the higher-order structure as well as the difference in the functions due to the foregoing structural differences.

In addition, the emitting layer may likewise be prepared by a method comprising preparing a solution of a binder such as a resin and a raw compound by dissolving them in a solvent and then forming a thin film using the resulting solution according to the spin coating method or the like, as disclosed in J.P. KOKAI Sho 57-51781.

In the present invention, the emitting materials or the host materials usable in the emitting layer include, for instance, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole-chelated oxinoid compounds, quinacridone, rubrene, and fluorescent dyes, but the materials is not limited to these specific examples.

In the present invention, the novel compounds according to the present invention may be used as emitting materials. In this case, without departing from the object according to the present invention, an emitting layer to be formed may contain, as necessary, any known emitting material other than the emitting materials made of the novel compounds according to the present invention. Moreover, an emitting layer containing such other known emitting material may be stacked on the emitting layer containing the emitting material made of the novel compound according to the present invention.

The emitting materials or the doping materials usable in the emitting layer together with the novel compounds according to the present invention include the materials given previously as the emitting materials or the host materials usable in the emitting layer.

As the host materials usable in the emitting layer together with the novel compounds according to the present invention, or together with the emitting materials, preferably used herein are compounds represented by the following general formulas (i) to (ix).

Asymmetric anthracenes represented by the following general formula (1):

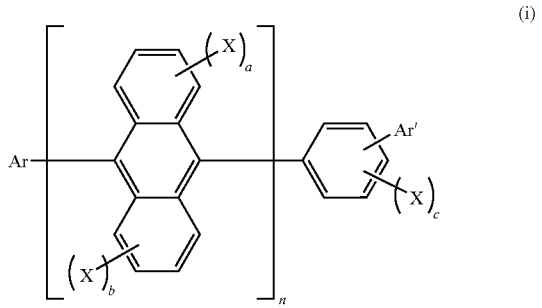

wherein Ar is a substituted or unsubstituted fused aromatic group having 10 to 50 of the number of carbon atoms forming the aromatic ring;

Ar' is a substituted or unsubstituted aromatic group having 6 to 50 ring carbon atoms;

X is a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group, or a hydroxyl group;

a, b, and c each represent an integer of 0 to 4; and n is an integer of 1 to 3, provided that if n is 2 or more, groups in the square brackets [ ] may be the same or different.

Asymmetric monoanthracene derivatives represented by the following general formula (ii):

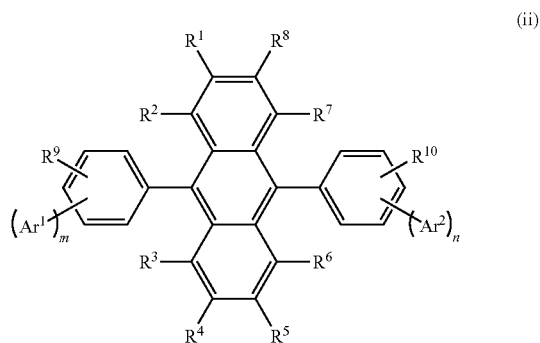

wherein $Ar^1$ and $Ar^2$ each independently represent a substituted or unsubstituted aromatic ring group having 6 to 50 ring carbon atoms, and m and n each represent an integer of 1 to 4, provided that, when m=n=1 and binding positions of $Ar^1$ and $Ar^2$ to the corresponding benzene rings are bilaterally symmetric, $Ar^1$ and $Ar^2$ are not the same, and provided that, when m or n is an integer of 2 to 4, m and n are integers different from each other;

$R^1$ to $R^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group.

Asymmetric pyrene derivatives represented by the following general formula (iii):

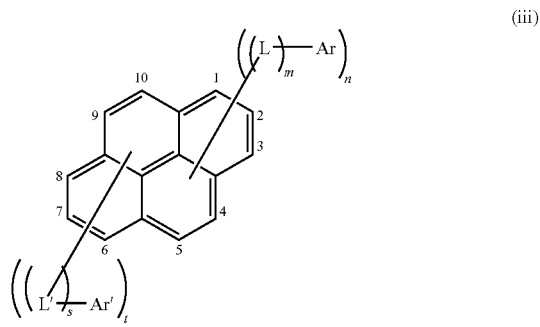

wherein Ar and Ar' each represent a substituted or unsubstituted aromatic group having 6 to 50 ring carbon atoms;

L and L' each represent a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2, n represents an integer of 1 to 4, s represents an integer of 0 to 2, and t represents an integer of 0 to 4; and L or Ar is bonded to any one of the 1- to 5-positions of pyrene, and also L' or Ar' is bonded to any one of the 6- to 10-positions of pyrene, provided that, when n+t is an even number, Ar, Ar', L, and L' satisfy the following requirement (1) or (2):

(1) Ar≠Ar' and/or L≠L' (where ≠ indicates each group has a different structure)

(2) when Ar=Ar' and L=L', (2-1) m≠s and/or n≠t, or (2-2) when m=s and n=t, (2-2-1) L and L', or pyrene are bonded respectively to different bonding positions of Ar and Ar', or (2-2-2) when L and L', or pyrene are bonded to the same bonding position of Ar and Ar', a case is excluded where the substitution positions of L and L', or Ar and Ar' on pyrene respectively are the 1-position and the 6-position thereof, or the 2-position and the 7-position.

Asymmetric anthracene derivatives represented by the following general formula (Iv):

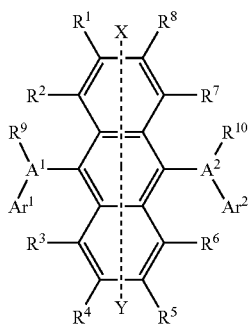

(iv)

wherein $A^1$ and $A^2$ each independently represent a substituted or unsubstituted fused aromatic ring group having 10 to 20 ring carbon atoms;

$Ar^1$ and $Ar^2$ each independently represent a hydrogen atom or a substituted or unsubstituted aromatic ring group having 6 to 50 ring carbon atoms;

$R^1$ to $R^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group; and $Ar^1$, $Ar^2$, $R^9$, and $R^{10}$ may each represent multiple groups, and those thereof, adjacent to one another, may form a saturated or unsaturated ring structure;

however, a case is excluded where, in the general formula (iv), groups symmetric with each other with respect to the axis X-Y shown in the anthracene at the center are bonded respectively at the 9- and 10-positions of the anthracene. Anthracene derivatives represented by the following general formula (v):

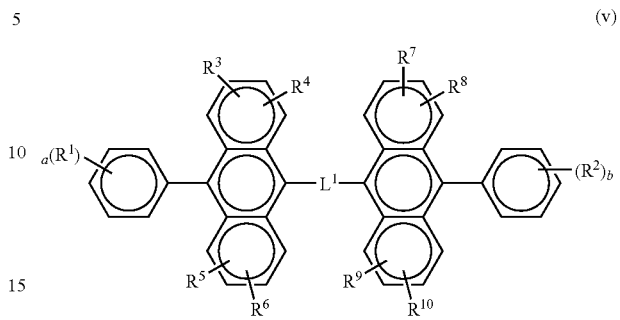

(v)

wherein $R^1$ to $R^{10}$ each independently represent a hydrogen atom, an alkyl group, a cycloalkyl group, an aryl group, which may be substituted, an alkoxyl group, an aryloxy group, an alkylamino group, an alkenyl group, an arylamino group, or a heterocyclic group, which may be substituted, and a and b each represent an integer of 1 to 5, provided that, when any of a and b is 2 or more, the groups represented by $R^1$ or $R^2$ may be the same or different, the groups of $R^1$ or of $R^2$ may be linked together to form a ring, and the pair of $R^3$ and $R^4$, the pair of $R^5$ and $R^6$, the pair of $R^7$ and $R^8$, or the pair of $R^9$ and $R^{10}$ may be linked together to form a ring; and $L^1$ represents a single bond, —O—, —S—, —N(R)— (in which R represents an alkyl group or an aryl group which may be substituted,), an alkylene group, or an arylene group. Anthracene derivatives represented by the following general formula (vi):

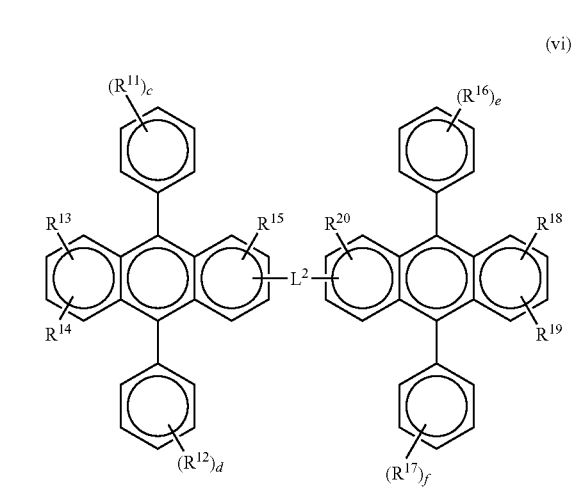

(vi)

wherein $R^{11}$ to $R^{20}$ each independently represent a hydrogen atom, an alkyl group, a cycloalkyl group, an aryl group, an alkoxy group, an aryloxy group, an alkylamino group, an arylamino group, or a polycyclic group, which may be substituted; and c, d, e, and f each represent an integer of 1 to 5, provided that, when any of these integers is 2 or more, these groups of $R^{11}$, of $R^{12}$, of $R^{16}$, or of $R^{17}$ may be the same or different, and also these groups of $R^{11}$, of $R^{12}$, of $R^{16}$, or of $R^{17}$ may be linked together to form a ring, and further, the pair of $R^{13}$ and $R^{14}$, or the pair of $R^{18}$ and $R^{19}$ may be linked together to form a ring; and wherein $L^2$ represents a single bond, —O, —S—, N(R)— (in which R represents an alkyl group or an aryl group, which may be substituted), an alkylene group, or an arylene group.

Spirofluorene derivatives represented by the following general formula (vii):

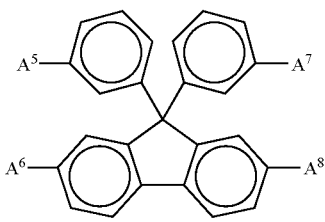

(vii)

wherein $Ar^5$ to $A^8$ each independently represent a substituted or unsubstituted biphenyl group, or a substituted or unsubstituted naphthyl group.

Fused ring-containing compounds represented by the following general formula (viii):

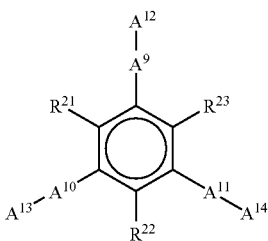

(viii)

wherein $A^9$ to $A^{14}$ are the same as those described above; $R^{21}$ to $R^{23}$ each independently represent a hydrogen atom, an alkyl group having 1 to 6 carbon atoms, a cycloalkyl group having 3 to 6 carbon atoms, an alkoxy group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms, or a halogen atom, provided that at least one of $A^9$ to $A^{14}$ is a group having three or more fused aromatic rings.

Fluorene compounds represented by the following general formula (ix):

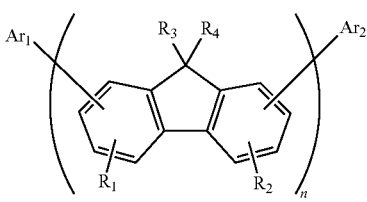

(ix)

wherein $R_1$ and $R_2$ each represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, provided that the groups represented by $R_1$ bonded respectively to two different fluorene groups may be the same or different and the groups represented by $R_2$ of two different fluorene groups may be the same or different, and that the groups represented respectively by $R_1$ and $R_2$ bonded to the same fluorene group may be the same or different; $R_3$ and $R_4$ each represent a hydrogen atom, a substituted or unsubstituted alkyl group, a substituted or unsubstituted aralkyl group, a substituted or unsubstituted aryl group, or a substituted or unsubstituted heterocyclic group, provided that the groups represented by $R_3$ bonded respectively to two different fluorene groups may be the same or different and the groups represented by $R_4$ of two different fluorene groups may be the same or different, and that the groups represented respectively by $R_3$ and $R_4$ bonded to the same fluorene group may be the same or different; $Ar_1$ and $Ar_2$ each represent a substituted or unsubstituted fused polycyclic aromatic group having three or more benzene rings in total, or a substituted or unsubstituted fused polycyclic heterocyclic group having three or more of benzene rings and heterocyclic rings in total and bonded to a fluorene group via a carbon atom, provided that $Ar_1$ and $Ar_2$ may be the same or different; and n represents an integer of 1 to 10.

Among these above-described host materials, preferably used herein are the anthracene derivatives, more preferably used herein are the monoanthracene derivatives, and particularly preferably used herein are the asymmetric anthracenes.

In addition, as the emitting material which is the dopant, a phosphorescence emitting compound may be used. As the host material for such phosphorescence emitting compound, preferably used herein is a compound having a carbazole ring.

The host made of a compound containing a carbazole ring and suitably used for the phosphorescent emission is a compound having a function to cause light emission of a phosphorescent emitting compound as a result of the transfer of energy to the phosphorescent emitting compound from the host compound in the excited state. The host compound is not particularly limited as long as the host compound is capable of transferring the exciton energy to the phosphorescent emitting compound, and thus may be selected as appropriate. The host compound may have any desired heterocyclic ring or the like in addition to the carbazole ring.

Specific examples of the above host compound include: carbazole derivatives; triazole derivatives; oxazole derivatives; oxadiazole derivatives; imidazole derivatives; polyarylalkane derivatives; pyrazoline derivatives; pyrazolone derivatives; phenylenediamine derivatives; arylamine derivatives; amino-substituted chalcone derivatives; styrylanthracene derivatives; fluorenone derivatives; hydrazone derivatives; stilbene derivatives; silazane derivatives; aromatic tertiary amine derivatives; styrylamine derivatives; aromatic dimethylidene compounds; porphyrin compounds; anthraquinonedimethane derivatives; anthrone derivatives; diphenylquinone derivatives; thiopyran dioxide derivatives; carbodiimide derivatives; fluorenylidenemethane derivatives; distyrylpyrazine derivatives; heterocyclic tetracarboxylic anhydrides such as naphthaleneperylene; various metal complex represented by metal complexes of phthalocyanine derivatives and 8-quinolinol derivatives, metal phthalocyanines, and metal complexes comprising, benzoxazole and benzothiazole as ligands; polysilane compounds; and high molecular compounds including poly(N-vinylcarbazole) derivatives, aniline copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination of two or more kinds thereof.

The specific examples thereof include the following compounds:

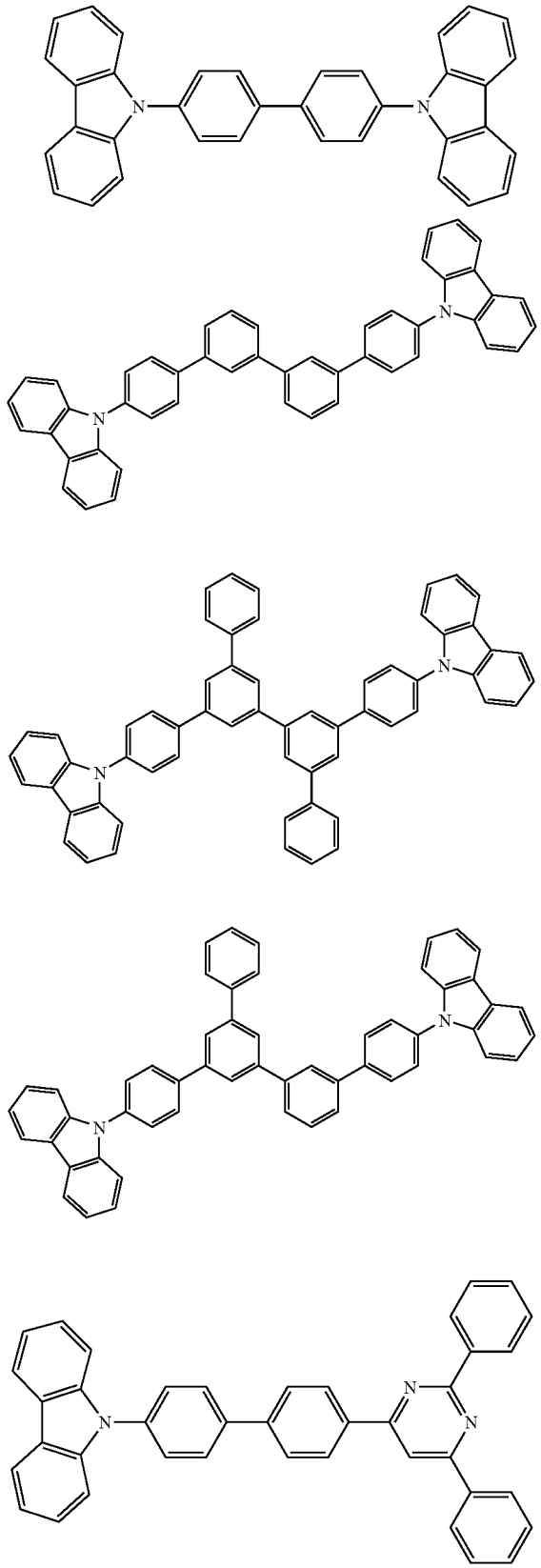

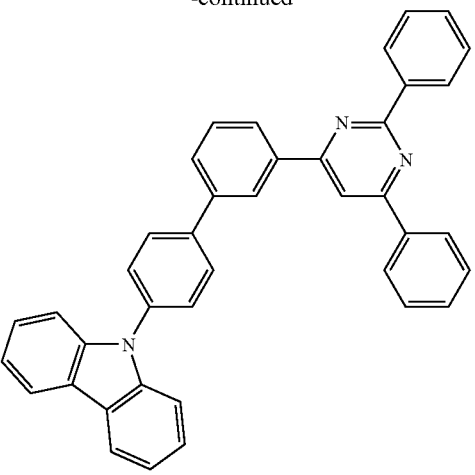

The phosphorescent emitting dopant is a compound capable of emitting light from a triplet exciton. The dopant is not particularly limited as long as the dopant is capable of emitting light from a triplet exciton, but preferably is a metal complex containing at least one metal selected from the group consisting of Ir, Ru, Pd, Pt, Os, and Re. As such metal complex, porphyrin metal complexes or ortho-metalated metal complexes are preferable. As the porphyrin metal complex, porphyrin platinum complexes are preferable. The phosphorescent emitting compounds may be used solely, or two or more of these may be used in combination.

There are various ligands capable of forming the ortho-metalated metal complexes, preferable ligands used herein include 2-phenylpyridine derivatives, 7,8-benzoquinoline derivatives, 2-(2-thienyl)pyridine derivatives, 2-(1-naphthyl) pyridine derivatives, and 2-phenylquinoline derivatives. These derivatives may have a substituent when necessary. Particularly, fluorinated derivatives or derivatives comprising a trifluoromethyl group being introduced therein are preferable as a blue dopant. The ortho-metalated metal complexes to be used herein may further have, as an auxiliary ligand, a ligand such as acetylacetonato or picric acid, other than those listed above.

The content ratio of the phosphorescent emitting dopant in the emitting layer is not particularly limited and may be selected according to its object, but may be, for example, 0.1 to 70% by mass, and preferably is 1 to 30% by mass. If the content ratio of the phosphorescent emitting compound is below 0.1% by mass, the emission of light is weak, so that the effect obtained by the compound is not sufficiently exerted. If the content ratio exceeds 70% by mass, a phenomenon called concentration quenching becomes prominent, so that the element performance is deteriorated.

Meanwhile, the emitting layer may comprise a hole transporting material, an electron transporting material, or a polymer binder, as needed.

In addition, the thickness of the emitting layer is preferably 5 to 50 nm, more preferably 7 to 50 nm, most preferably 10 to 50 nm. If the thickness is below 5 nm, the formation of the emitting layer is difficult, so that the control of chromaticity may possibly become difficult. If the thickness exceeds 50 nm, the driving voltage may possibly increase.

(Hole Injecting and Transporting Layer (Hole Transporting Zone))

The hole injecting and transporting layer is a layer for helping the injection of holes into the emitting layer and for transporting the holes to the emitting zone, and has a high hole mobility and in general a low ionization energy which is 5.5 eV or less. A material for such a hole injecting and transporting layer is preferably a material which permits the transportation of holes to the emitting layer at a lower electric field strength and further preferably, for instance, a material which has at least $10^{-4}$ cm$^2$/V·s of the hole mobility when applying an electric field of $10^4$ to $10^6$ V/cm to the layer.

When the novel compound according to the present invention is used in the hole transporting zone, the hole injecting and transporting layer may be formed from the novel compound according to the present invention alone or in combination with another material. The material used for forming the hole injecting and transporting layer in combination with the novel compound according to the present invention is not limited to any specific one as long as it has the above preferred characteristic properties and thus can be selected from the group consisting of the conventional hole transporting materials currently used in the photoconductive materials and known materials for a hole injecting and transporting layer of organic EL devices.

Specific examples of such materials used for forming the hole injecting and transporting layer in combination with the novel compound according to the present invention include triazole derivatives (see, for instance, U.S. Pat. No. 3,112,197); oxadiazole derivatives (see, for instance, U.S. Pat. No. 3,189,447); imidazole derivatives (Japanese Examined Patent Publication (hereunder referred to as "J.P. KOKOKU") Sho 37-16096); polyarylalkane derivatives (see, for instance, U.S. Pat. Nos. 3,615,402, 3,820,989 and 3,542,544; J.P KOKOKU Nos. Sho 45-555 and Sho 51-10983; and J.P. KOKAI Nos. Sho 51-93224, Sho 55-17105, Sho 56-4148, Sho 55-108667, Sho 55-156953 and Sho 56-36656); pyrazoline derivatives and pyrazolone derivatives (see, for instance, U.S. Pat. Nos. 3,180,729 and 4,278,746; and J.P. KOKAI Nos. Sho 55-88064, Sho 55-88065, Sho 49-105537, Sho 55-51086, Sho 56-80051, Sho 56-88141, Sho 57-45545, Sho 54-112637 and Sho 55-74546); phenylenediamine derivatives (see, for instance, U.S. Pat. No. 3,615,404; and J.P. KOKOKU Nos. Sho 51-10105, Sho 46-3712 and Sho 47-25336; and J.P. KOKAI Nos. Sho 54-110536 and Sho 54-119925); arylamine derivatives (see, for instance, U.S. Pat. Nos. 3,567,450, 3,180,703, 3,240,597, 3,658,520, 4,232,103, 4,175,961 and 4,012,376; J.P. KOKOKU Nos. Sho 49-35702 and Sho 39-27577; J.P. KOKAI Nos. Sho 55-144250, Sho 56-119132 and Sho 56-22437; and German Patent No. 1,110,518); amino-substituted chalcone derivatives (see, for instance, U.S. Pat. No. 3,526,501); oxazole derivatives (such as those disclosed in, for instance, U.S. Pat. No. 3,257,203); styrylanthracene derivatives (see, for instance, J.P. KOKAI No. Sho 56-46234); fluorenone derivatives (see, for instance, J.P. KOKAI No. Sho 54-110837); hydrazone derivatives (see, for instance, U.S. Pat. No. 3,717,462; and J.P. KOKAI Nos. Sho 54-59143, Sho 55-52063, Sho 55-52064, Sho 55-46760, Sho 57-11350, Sho 57-148749, and Hei 2-311591); stilbene derivatives (see, for instance, J.P. KOKAI Nos. Sho 61-210363, Sho 61-228451, Sho 61-14642, Sho 61-72255, Sho 62-47646, Sho 62-36674, Sho 62-10652, Sho 62-30255, Sho 60-93455, Sho 60-94462, Sho 60-174749 and Sho 60-175052); silazane derivatives (see, for instance, U.S. Pat. No. 4,950,950); polysilane type (see J.P. KOKAI No. Hei 2-204996); and aniline copolymers (see J.P. KOKAI No. Hei 2-282263); and conducting high molecular weight oligomers disclosed in J.P. KOKAI Hei 1-211399 (in particular, thiophene oligomers).

Although the materials listed above can be used for the hole injecting and transporting layer, porphyrin compounds (such as those disclosed in, for instance, J.P. KOKAI No. Sho 63-295695); aromatic tertiary amine compounds and styrylamine compounds (see, for instance, U.S. Pat. No. 4,127,412; and J.P. KOKAI Nos. Sho 53-27033, Sho 54-58445, Sho 54-149634, Sho 54-64299, Sho 55-79450, Sho 55-144250, Sho 56-119132, Sho 61-295558, Sho 61-98353 and Sho 63-295695), in particular, aromatic tertiary amine compounds are preferable.

In addition, materials for the hole injecting and transporting layer includes compounds each having two fused aromatic rings in the molecule as disclosed in U.S. Pat. No. 5,061,569 such as 4,4'-bis(N-(1-naphthyl)-N-phenylamino) biphenyl (hereunder abbreviated as "NPD") and those disclosed in J.P. KOKAI Hei 4-308688 such as 4,4',4"-tris(N-(3-methylphenyl)-N-phenylamino)triphenylamine (hereunder abbreviated as "MTDATA") in which three triphenylamine units are connected in the form of a star burst-like shape.

In addition to the aromatic dimethylidine type compounds already described above as the materials for the emitting layer, inorganic compounds such as p-type Si and p-type SiC can likewise be used as materials for the hole injecting and transporting layer.

The hole injecting and transporting layer can be prepared by forming the novel compound according to the present invention into a thin film according to any known methods such as the vacuum evaporation method, the spin coating method, the casting method, and the LB method. The thickness of the hole injecting and transporting layer is not limited to any particular level, but it in general ranges from 5 nm to 5 μm. This hole injecting and transporting layer may comprise a single layer containing one or at least two kinds of the foregoing materials, or it may be a laminate with a hole injecting and transporting layer comprising a compound different from that used for forming the foregoing hole injecting and transporting layer as long as the hole transporting zone contains the novel compound according to the present invention.

In addition, it is also possible to form an organic semiconductor layer as a layer for helping the hole injection or electron injection into the emitting layer and the organic semiconductor layer preferably has $10^{-10}$ S/cm or more of the conductivity. Materials for such an organic semiconductor layer include conductive oligomers such as thiophene-containing oligomers and arylamine-containing oligomers as those disclosed in J.P. KOKAI Hei 8-193191; and conducting dendrimers such as arylamine-containing dendrimers.

(Electron Injecting and Transporting Layer)

The electron injecting and transporting layer is a layer for helping the injection of electrons into the emitting layer and for transporting the electrons to the emitting zone, and has a high electron mobility, while an adhesion improving layer is one of the electron injecting layers, which consists of a material excellent in the adhesion to the cathode.

Moreover, it is known that, since emitted light is reflected by an electrode (the cathode in this case) in the organic EL device, the light emission directly taken out through the anode and the light emission taken out by means of the reflection by the electrode interfere with each other. In order to efficiently utilize the effect of interference, the thickness of the electron transporting layer is selected from a range from several nm to several μm as appropriate. Particularly when the thickness is large, the electron transporting layer has preferably at least $10^{-5}$ cm$^2$/V·s of the electron mobility when applying an electric field of $10^4$ to $10^6$ V/cm to the layer in order to avoid the voltage increase.

As the material for the electron injecting layer, preferably used herein are metal complexes of 8-hydroxyquinoline or the derivatives thereof and oxadiazole derivatives. Specific examples of metal complexes of 8-hydroxyquinoline or the derivatives thereof are metal chelated oxinoid compounds including chelates of oxine (in general, 8-quinolinol or 8-hydroxyquinoline). For instance, tris(8-quinolinol)aluminum can be used as an electron injecting material.

On the other hand, the oxadiazole derivatives include the electron transport compounds represented by the following general formulas:

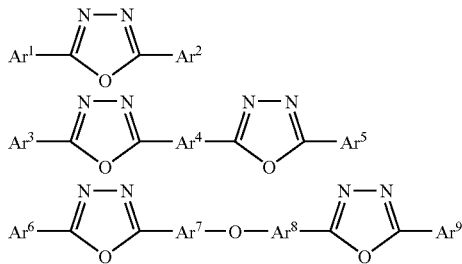

wherein Ar$^1$, Ar$^2$, Ar$^3$, Ar$^5$, Ar$^6$ and Ar$^9$, which may be the same or different, each represent a substituted or unsubstituted aryl group; and Ar$^4$, Ar$^7$ and Ar$^8$, which may be the same or different, each represent a substituted or unsubstituted arylene group.

In this connection, such aryl groups include phenyl, biphenyl, anthranyl, perylenyl, and pyrenyl groups. Moreover, such arylene groups include phenylene, naphthylene, biphenylene, anthranylene, perylenylene, and pyrenylene groups. Moreover, substituents of the foregoing aryl and arylene groups include an alkyl group each having 1 to 10 carbon atoms, an alkoxy group each having 1 to 10 carbon atoms and a cyano group. As such electron transport compounds, those having a thin film-forming ability is preferable.

Specific examples of the foregoing electron transport compounds include those listed below:

Moreover, as the material used for the electron injecting layer and the electron transporting layer, compounds represented by the following general formulas (A) to (F) may be used:

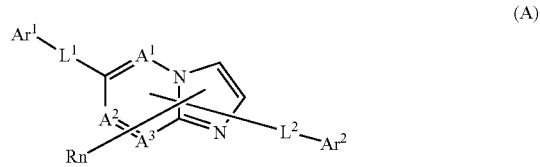

(A)

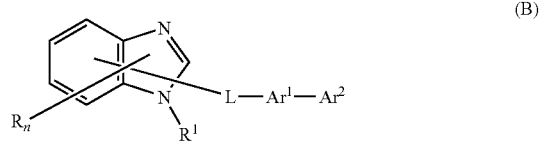

(B)

wherein A$^1$ to A$^3$ each independently represent a nitrogen atom or a carbon atom; Ar$^1$ represents a substituted or unsubstituted aryl group having 6 to 60 ring carbon atoms, or a substituted or unsubstituted heteroaryl group having 3 to 60 ring carbon atoms; Ar$^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or a divalent group of any of these listed above, provided that one of Ar$^1$ and Ar$^2$ is a substituted or unsubstituted fused ring group having 10 to 60 ring carbon atoms or a substituted or unsubstituted monohetero fused ring group having 3 to 60 ring carbon atoms;

L$^1$, L$^2$, and L each independently represent a single bond, a substituted or unsubstituted arylene group having 6 to 60 ring carbon atoms, a substituted or unsubstituted heteroarylene group having 3 to 60 ring carbon atoms, or a substituted or unsubstituted fluorenylene group;

R represents, a hydrogen atom, a substituted or unsubstituted aryl group having 6 to 60 ring carbon atoms, a substi-

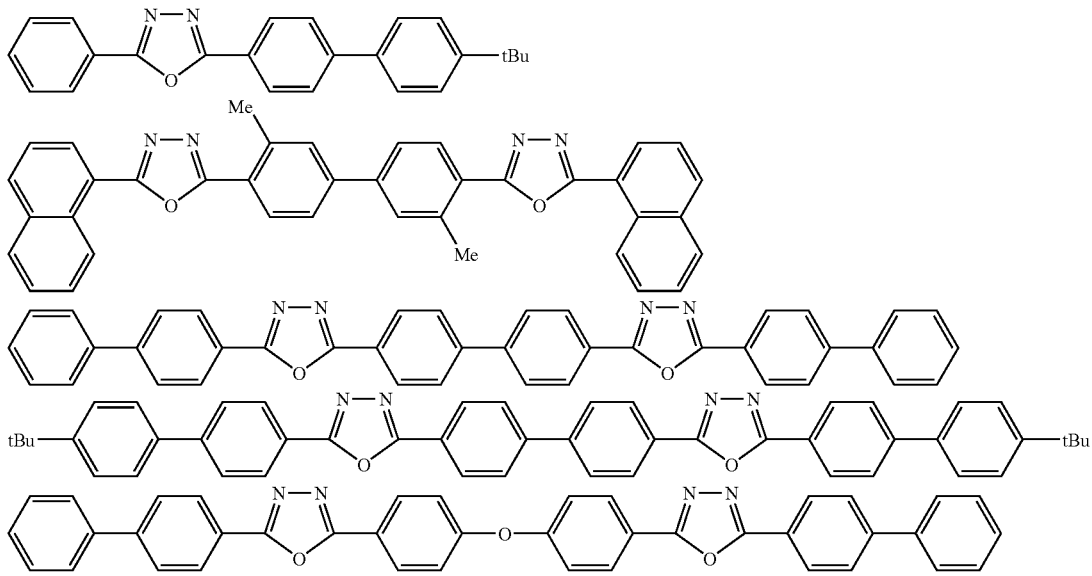

tuted or unsubstituted heteroaryl group having 3 to 60 ring carbon atoms, a substituted or unsubstituted alkyl group having 1 to 20 carbon atoms, and a substituted or unsubstituted alkoxy group having 1 to 20 carbon atoms;

n represents an integer of 0 to 50, provided that, when n is 2 or more, multiple groups each represented by R may be the same or different, and those, adjacent to each other, of these multiple R groups may be linked together to form a carbocyclic aliphatic ring or a carbocyclic aromatic ring.

$$HAr-L-Ar^1—Ar^2 \quad (C)$$

wherein HAr represents a nitrogen-containing heterocyclic ring which has 3 to 40 carbon atoms and which may have a substituent; L represents a single bond, an arylene group which has 6 to 60 carbon atoms and which may have a substituent, a heteroarylene group which has 3 to 60 carbon atoms and which may have a substituent, or a fluorenylene group which may have a substituent; $Ar^1$ represents a divalent aromatic hydrocarbon group which has 6 to 60 carbon atoms and which may have a substituent; and $Ar^2$ represents an aryl group which has 6 to 60 carbon atoms and which may have a substituent, or a heteroaryl group which has 3 to 60 carbon atoms and which may have a substituent.

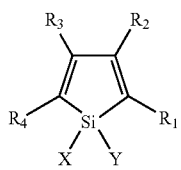

(D)

wherein X and Y each independently represent a saturated or unsaturated hydrocarbon group having 1 to 6 carbon atoms, an alkoxy group, an alkenyloxy group, an alkynyloxy group, a hydroxy group, a substituted or unsubstituted aryl group, a substituted or unsubstituted heterocyclic ring, or X and Y are linked together to form a saturated or unsaturated ring structure; $R_1$ to $R_4$ each independently represent a hydrogen atom, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group; or if any of $R_1$ to $R_4$ are adjacent to each other, these adjacent groups form a structure in which a substituted or unsubstituted ring is fused.

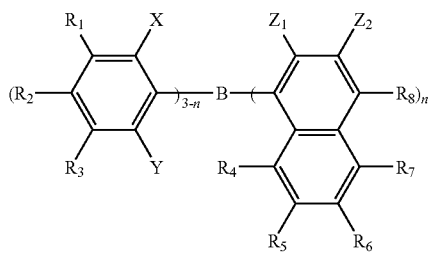

(E)

wherein $R_1$ to $R_8$ and $Z_2$ each independently represent a hydrogen atom, a saturated or unsaturated hydrocarbon group, an aromatic group, a heterocyclic group, a substituted amino group, a substituted boryl group, an alkoxy group, or an aryloxy group; X, Y, and $Z_1$ each independently represent a saturated or unsaturated hydrocarbon group, an aromatic group, a heterocyclic group, a substituted amino group, an alkoxy group, or an aryloxy group, provided that substituents of $Z_1$ and $Z_2$ may be linked to form a fused ring; n represents an integer of 1 to 3, provided that when n represents 2 or more, the groups represented by $Z_1$ may be different, provided that a case where n represents 1, X, Y, and $R_2$ each represent a methyl group, and $R_8$ represents a hydrogen atom or a substituted boryl group, and a case where n represents 3 and $Z_1$ represents a methyl group are excluded.

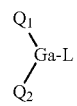

(F)

wherein $Q^1$ and $Q^2$ each independently represent a ligand represented by the following general formula (G); L represents a halogen atom, a substituted or unsubstituted alkyl group, a substituted or unsubstituted cycloalkyl group, a substituted or unsubstituted aryl group, a substituted or unsubstituted heterocyclic ring group, —$OR^1$ ($R^1$ represents a hydrogen atom, a substituted or unsubstituted alkyl group, a substituted or unsubstituted cycloalkyl group, a substituted or unsubstituted aryl group, or a substituted or unsubstituted heterocyclic ring group), or a ligand represented by —O—Ga-$Q^3$ ($Q^4$) ($Q^3$ and $Q^4$ are the same as $Q^1$ and $Q^2$, respectively).

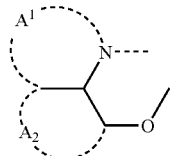

(G)

wherein each of the rings $A^1$ and $A^2$ represents a six-membered fused aryl cyclic structure which may have a substituent.

This metal complex has strong properties as an n-type semiconductor and thus has high electron-injecting ability. Moreover, since the metal complex has a low production energy when being formed, the bonding characteristic of the metal of the formed metal complex with the ligand is strong, thus having a high fluorescence quantum efficiency as an emitting material.

Specific examples of the substituents of the rings $A^1$ and $A^2$ forming the ligands represented by the general formula (G) include: halogen atoms, such as a chlorine atom, a bromine atom, an iodine atom, and a fluorine atom; substituted or unsubstituted alkyl groups, such as a methyl group, an ethyl group, a propyl group, a butyl group, a sec-butyl group, a t-butyl group, a pentyl group, a hexyl group, a heptyl group, an octyl group, a stearyl group, and a trichloromethyl group; substituted or unsubstituted aryl groups, such as a phenyl group, a naphthyl group, a 3-methylphenyl group, a 3-methoxyphenyl group, a 3-fluorophenyl group, a 3-trichloromethylphenyl group, a 3-trifluoromethylphenyl group, and a 3-nitrophenyl group; substituted or unsubstituted alkoxy groups, such as a methoxy group, an n-butoxy group, t-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group, and a 6-(perfluoroethyl)hexyloxy group; substituted or unsubstituted aryloxy groups, such as a phenoxy group, a p-nitrophenoxy group, a p-t-butylphenoxy group, a 3-fluorophenoxy group, a pentafluorophenyl group, and a 3-trifluoromethylphenoxy group; substituted or unsubstituted alkylthio groups, such as a methylthio group, an ethylthio group, a t-butylthio group, a hexylthio group, an octylthio group, a trifluoromethylthio group, and a 3-trifluoromethylphenylthio group; substituted or unsubstituted arylthio groups, such as a phenylthio group, a p-nitrophenylthio group, a p-t-butylphenylthio group, a 3-fluorophenylthio group, a pentafluorophenylthio group, and a 3-trifluoromethylphenylthio group; a cyano group; a nitro group; mono- or di-substituted amino groups, such as an amino group, a methylamino group, a diethylamino group, an ethylamino group, a diethylamino group, a dipropylamino group, a dibutylamino group, and a diphenylamino group; acylamino groups, such as a bis(acetoxymethyl)amino group, a bis(acetoxyethyl)amino group, bis(acetoxypropyl)amino group, and a bis(acetoxybutyl)amino group; a hydroxyl group, a siloxy group; acyl groups; carbamoyl groups, such as a methylcarbamoyl group, a dimethylcarbamoyl group, an ethylcarbamoyl group, diethylcarbamoyl group, a propylcarbamoyl group, a butylcarbamoyl group, and a phenylcarbamoyl group; a carboxyl acid group; a sulfonic acid group; an imide group; cycloalkyl groups, such as a cyclopentane group and a cyclohexyl group; aryl groups, such as a phenyl group, a naphthyl group, a biphenyl group, an anthranil group, a phenanthryl group, a fluorenyl group, and a pyrenyl group; heterocyclic groups, such as a pyridinyl group, pyradinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morphodinyl group, a piperazinyl group, a triatinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, a pranyl group. Moreover, those of the above-listed substituents may be linked together to further form a six-membered aryl ring or a heterocyclic ring.

A preferred mode of the organic EL device according to the present invention is a device containing a reducing dopant in a region for transferring electrons, or the boundary region between the cathode and the organic layer. Here, the reducing dopant is defined as a substance that is capable of reducing an electron transport compound. Accordingly, any of various kinds of reducing dopants may be used as long as the dopant has certain reducibility. For example, preferably used herein is at least one substance selected from the group consisting of alkali metals, alkaline earth metals, rare earth metals, alkali metal oxides, alkali metal halides, alkaline earth metal oxides, alkaline earth metal halides, rare earth metal oxides and rear earth metal halides, organic complexes of alkali metals, organic complexes of alkaline earth metals, and organic complexes of rear earth metals.

More specifically, the foregoing reducing dopants preferably used in the present invention include at least one alkali metal selected from the group consisting of Li (Work Function: 2.9 eV), Na (Work Function: 2.36 eV), K (Work Function: 2.28 eV), $R^b$ (Work Function: 2.16 eV) and Cs (Work Function: 1.95 eV); and at least one alkaline earth metal selected from the group consisting of Ca (Work Function: 2.9 eV), Sr (Work Function: 2.0 to 2.5 eV) and Ba (Work Function: 2.52 eV), with those having 2.9 eV or less of the work function being particularly preferably. Among them, more preferably used herein as the reducing dopants are at least one alkali metal selected from the group consisting of Li, K, Rb and Cs, further preferably used herein are Rb and Cs, and most preferably used herein is Cs. These alkali metals show a particularly high reducing ability and would thus permit the improvement of the luminance of the emitted light and the substantial extension of the lifetime of the resulting organic EL device through the addition thereof to the electron injecting zone even in a relatively small quantity. Moreover, as the reducing dopant having a work function of 2.9 eV or less, a combination of two or more of these alkali metals is also preferable, and in particular, a combination including Cs, for example, a combination of Cs and Na, of Cs and K, of Cs and Rb, or of Cs and Na and K, is preferable. The reducing dopant including Cs in combination can exert sufficiently high reducing ability, and accordingly, makes it possible to achieve the improvement of the luminance of the emitted light and the substantial extension of the lifetime of the resulting organic EL device through the addition of such reducing dopant to the electron injecting zone.

In the present invention, an electron injecting layer composed of an insulating material or a semiconductor material may further provided between the cathode and the organic layer. Providing the electron injecting layer makes it possible to effectively prevent leakage of the electric current, and to thus improve the electron injection efficiency. As such insulating materials, preferably used herein is at least one metal compound selected from the group consisting of alkali metal chalcogenides, alkaline earth metal chalcogenides, alkali metal halides, and alkaline earth metal halides. It is preferable that the electron injecting layer be composed of any of these alkali metal chalcogenides and the like because such electron injecting layer further improves the electron injection efficiency. Specific examples of the alkali metal chalcogenides preferably used herein include $Li_2O$, $K_2O$, $Na_2S$, $Na_2Se$, and $Na_2O$. The alkaline earth metal chalcogenides preferably used herein include CaO, BaO, SrO, BeO, BaS, and CaSe. In addition, the alkali metal halides preferably used herein include LiF, NaF, KF, LiCl, KCl, NaCl, and the like. Moreover, the alkaline earth metal halides preferably used herein include: fluorides such as $CaF_2$, $BaF_2$, $SrF_2$, $MgF_2$, and $BeF_2$; and halides other than fluorides.

On the other hand, as the aforementioned semiconductor materials constituting the electron transporting layer, used herein is one of, or a combination of two or more of, oxides, nitrides, and oxynitrides, each containing at least one element of Ba, Ca, Sr, Yb, Al, Ga, In, Li, Na, Cd, Mg, Si, Ta, Sb, and Zn. In addition, it is preferable that the inorganic compound constituting the electron transporting layer form a microcrystalline or amorphous insulating thin film. If the electron transporting layer is formed of such insulating thin film, a more uniform thin film is formed, so that occurrence of pixel defects such as a dark sport can be reduced. Note that, such inorganic compounds include alkali metal chalcogenides, alkaline earth metal chalcogenides, alkali metal halides, and alkaline earth metal halides, all of which have been described above.

(Cathode)

As the cathode for injecting electrons to the electron injecting and transporting layer, or the emitting layer, used herein is one containing, as an electrode material, a metal, an alloy, an electrically-conductive compound, or a mixture of these substances, each having a small work function (4 eV or less). Specific examples of such electrode materials include sodium, a sodium-potassium alloy, magnesium, lithium, a magnesium-silver alloy, aluminum/aluminum oxide, an aluminum-lithium alloy, indium, rare earth metals, and the like.

This cathode may be prepared by forming such an electrode material into a thin film using the evaporation method, the sputtering method, or the like.

In this connection, in the case where the light emitted from the emitting layer is taken out through the cathode, the cathode preferably has over 10% of the transmittance for the light emitted from the emitting layer.

In addition, the cathode preferably has a sheet resistance of several hundred ($\Omega/\square$) or less. The cathode may usually have a thickness of 10 nm to 1 μm, and preferably of 50 to 200 nm.
(Insulating Layer)

In the organic EL device, an electric field is applied to an ultrathin film and accordingly, the device is subject to pixel defects due to any leakage or short circuit. To prevent such defects, it is preferable that an insulating thin film layer be interposed between the paired electrodes.

Examples of materials used for such an insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. It is also possible to use a mixture of or a laminate of the foregoing materials.
(Method for Preparation of Organic EL Device)

The organic EL device can be prepared by forming an anode, an emitting layer, a hole injecting and transporting layer as necessary, and an electron injecting and transporting layer as necessary; and further forming a cathode, using the materials and methods described above. Alternatively, the foregoing components may be formed in the reverse order starting from the cathode to the anode to thus forming an organic EL device.

Hereinafter, an example of forming an organic EL device having a structure in which an anode, a hole injecting layer, an emitting layer, an electron injecting layer, and a cathode are formed in this order on a light-transmissive substrate will be described.

First of all, a thin film made of an anode material is formed on an appropriate light-transmissive substrate so as to have a thickness of 1 μm or less, and preferably of 10 to 200 nm, by the evaporation method or the sputtering method, so that an anode is formed. Then, a hole injecting layer is formed on the anode. The hole injecting layer is formed by the vacuum evaporation method, the spin coating method, the casting method, or the LB method, as has been previously described, but the hole injecting layer is preferably formed by the vacuum evaporation method since a uniform film is easily obtained and a pinhole is unlikely to be formed, etc. When a hole injecting layer is formed by the vacuum evaporation method, the conditions for the evaporation may vary depending on the kind of compounds to be used (materials for the hole injecting layer) and the crystalline structure and recombined structure of the hole injecting layer to be formed, but in general, the vacuum evaporation method is preferably carried out under the following conditions: a temperature of the evaporation source of 50 to 450° C.; a degree of vacuum of $10^{-7}$ to $10^{-3}$ torr; an evaporation rate of 0.01 to 50 nm/sec; a substrate temperature of −50 to 300° C.; and a film thickness of 5 nm to 5 μm.

Subsequently, an emitting layer is formed on the hole injecting layer. The emitting layer may likewise be formed by forming a desired organic emitting material into a thin film by the vacuum evaporation method, the sputtering method, the spin coating method, the casting method, or the like; however, the emitting layer is preferably formed by the vacuum evaporation method since a uniform film is easily obtained and a pinhole is unlikely to be formed, etc. When the emitting layer is formed by the vacuum evaporation method, the conditions for the evaporation may vary depending on the kind of compounds to be used, but generally, the conditions can be selected from the same conditions as those for the hole injecting layer.

Next, an electron injecting layer is formed on the emitting layer. The electron injecting layer is preferably formed by the vacuum evaporation method since a uniform film should be formed, as in the cases of the hole injecting layer and the emitting layer. The conditions for the evaporation can be selected from the same conditions as those for the hole injecting layer and the emitting layer.

The aromatic amine derivative according to the present invention may be co-evaporated together with other materials when the vacuum evaporation method is used, although it depends on which layer, the emitting zone or the hole transporting zone, the aromatic amine derivative is incorporated into.

Moreover, when the spin coating method is used, the aromatic amine derivative may be incorporated into the layer by blending the aromatic amine derivative with another material.

Finally, a cathode is stacked to obtain an organic EL device.

The cathode is formed of a metal, and may be formed by the evaporation method or the sputtering method. However, the cathode is preferably formed by the vacuum evaporation method for the purpose of protecting the underlying organic layers from being damaged during the formation of the cathode film.

It is preferable that in the preparation of the organic EL device, the step of forming the anode to the step of forming the cathode be continuously carried out through a single vacuuming.

The method for forming each layer of the organic EL device according to the present invention is not particularly limited to any specific one. Any conventional forming method, such as the vacuum evaporation method, the spin coating method, or the like may be used. The organic thin film layer containing the compound represented by the foregoing general formula (1) used in the organic EL device according to the present invention can be formed by any known film-forming method, such as the vacuum evaporation method, the molecular beam evaporation method (MBE method), or application methods including the dipping method, the spin coating method, the casting method, the bar coating method, or the roll coating method, using a solution of the compound in a solvent.

The thickness of each organic layer in the organic EL device according to the present invention is not particularly limited. However, in general, if the thickness is too small, defects such as pinholes are likely to occur in the layer, while if the thickness is too large, the organic EL device requires a high voltage to be applied thereto for the operation, and thus the efficiency is reduced. For these reasons, usually, the thickness of each organic layer is preferably in a range from several nanometers to 1 μm.

In this connection, in a case where a DC voltage is applied to the organic EL device, emission of light can be observed when a voltage of 5 to 40 V is applied thereto and the polarity of the anode is made positive and the polarity of the cathode is made negative. On the other hand, any electric current never flows through the device when a voltage is applied thereto if the polarities of the anode and the cathode are reversed. Accordingly, no emission of light can be observed. In addition, in a case where an AC voltage is applied to the device, uniform emission of light can be observed only when the polarity of the anode is made positive and the polarity of the cathode is made negative. The alternating current to be applied to the device may have any wave form.

(Application of Organic EL Device)

The organic EL device according to the present invention can be applied to any products that should have a high luminance and a high luminous efficiency even with a low voltage applied thereto. Examples of application of the organic EL device according to the present invention include: display apparatuses, lighting apparatuses, light sources of printers, and backlights of liquid crystal display apparatuses, and the organic EL device according to the present invention may also be employed in the fields of signals, advertising displays, and interior. The display apparatuses include a flat panel display with low power consumption or high visibility. In addition, the light sources of printers include light sources of laser-beam printers. Further, using the device according to the present invention allows the volume of an apparatus to be considerably reduced. In respect of the lighting apparatus and backlights, it would be expected to achieve an energy saving effect through the use of the organic EL device according to the present invention.

The present invention will hereunder be described in more detail with reference to the following examples, but the present invention is by no means limited to these specific examples.

EXAMPLE

Example 1

Synthesis of Compound (I)

3 g of 3,3'-diaminobenzidine (a) and 6.13 g of 5,6-dichloro-2,3-dicyanopyrazine (b) were reacted in 150 ml of acetonitrile under heat reflux for 10 hours. The reaction fluid was filtered at room temperature, and the resulting solid phase was washed with 100 ml of acetonitrile, 200 ml of water, and 50 ml of MeOH. The resulting solids were dried at 40° C. under reduced pressure for 4 hours to obtain 3.13 g of a crude product (c). The crude product (c) was subjected to the mass spectrometry (FDMS) and found to have m/e=466, so that the crude product (c) was identified as the intended product.

Further, 3 g of the crude product (c) and 3.21 g of DDQ (d) were reacted in 150 ml of THF at room temperature for 7 hours. The resulting reaction fluid was filtered, and the resulting solids were washed with 100 ml of THF and 30 ml of hexane. The resulting solid was dried at 40° C. under reduced pressure for 4 hours to obtain 2.77 g of a compound The compound (I) was subjected to the mass spectrometry (FDMS) and thus found to have m/e=462, so that the compound (I) was identified as the intended product. The product was purified by the sublimation purification.

The compound was dissolved in acetonitrile at a concentration of 0.01 mol/liter, and the reduction potential thereof was measured according to the cyclic voltammetry using tetrabutylammonium perchorate (TBAP) as the supporting electrolyte and a silver-silver chloride electrode as the reference electrode. When the first oxidation potential of ferrocene (hereinafter referred to as "Fc") as the reference material was set as the reference, the reduction potential of the compound (1) was −0.36 V (vs Fc$^+$/Fc).

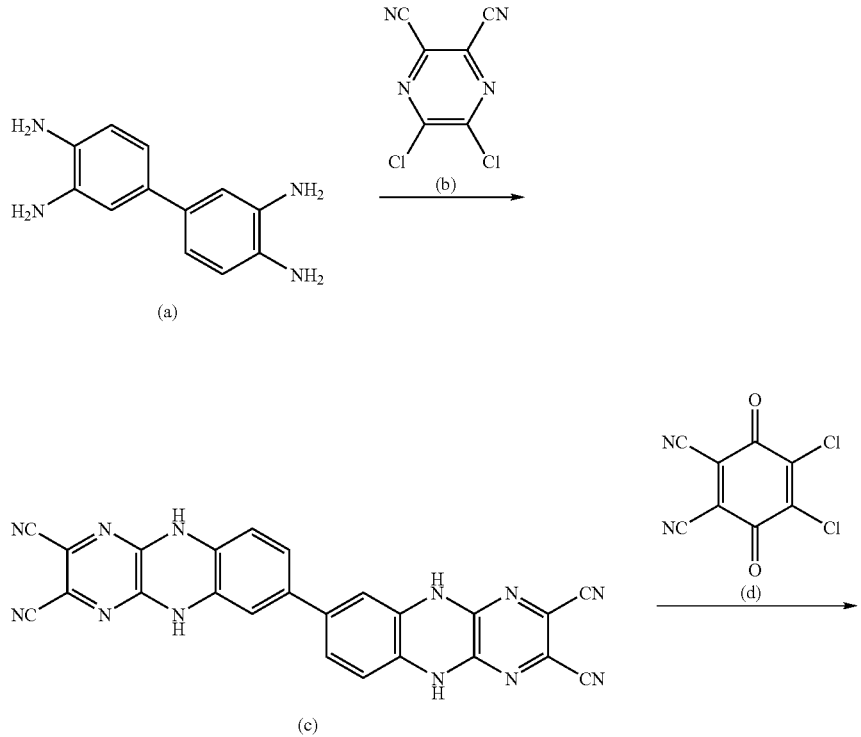

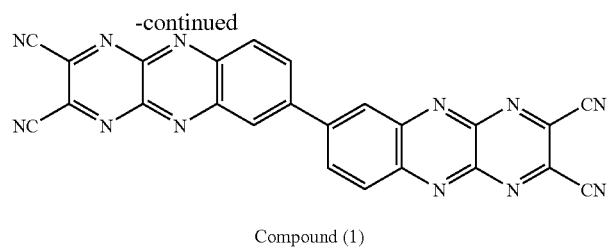

Compound (1)

Example 2

Synthesis of Compound (A-1)

10 g of acenaphthenequinone (e) and 8.8 g of 5,6-diamino-2,3-dicyanopyrazine (f) were reacted in 250 ml of pyridine under heat reflux for 18 hours. The reaction fluid was filtered at room temperature, and the resulting solid phase was washed with THF, and then further with acetonitrile. The resulting solids were dried at 60° C. under reduced pressure for 8 hours to obtain 11 g of a compound (A-1). The compound (A-1) was subjected to the mass spectrometry (FDMS) and found to have m/e=306, so that the compound (A-1) was identified as the intended product. The product was purified by the sublimation purification. The reduction potential of the purified compound was measured in the same manner as that for Example 1, and thereby found to be −0.48 V (vs Fc$^+$/Fc).

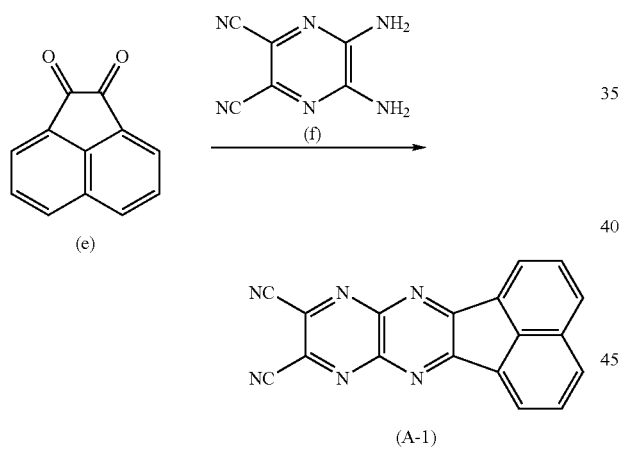

Example 3

Synthesis of Compound (3)

5 g of 4-trifluoromethyl-1,2-phenylenediamine (g) and 6.21 g of 5,6-dichloro-2,3-dicyanopyrazine (b) were reacted in 200 ml of acetonitrile under heat reflux for 10 hours. The reaction fluid was filtered at room temperature, and the resulting filtrate was concentrated to obtain 8.2 g of a crude product (h). The crude product (h) was subjected to the mass spectrometry (GC-MS) and found to have m/e=302, so that the crude product (h) was identified as the intended product. Further 6 g of the crude product (h) and 4.48 g of DDQ (d) were reacted in 100 ml of THF at room temperature for 8 hours. 400 ml of hexane was added to the resulting reaction fluid, and then a precipitate was collected by filtration. The resulting solids were dried at 60° C. under reduced pressure to obtain 3.33 g of a compound (3).

The compound (3) was subjected to the mass spectrometry (GC-MS) and found to have m/e=300, so that the compound (3) was identified as the intended product. The product was purified by the sublimation purification.

The reduction potential of the purified compound was measured in the same manner as that for Example 1, and thereby found to be −0.28 V (vs Fc$^+$/Fc).

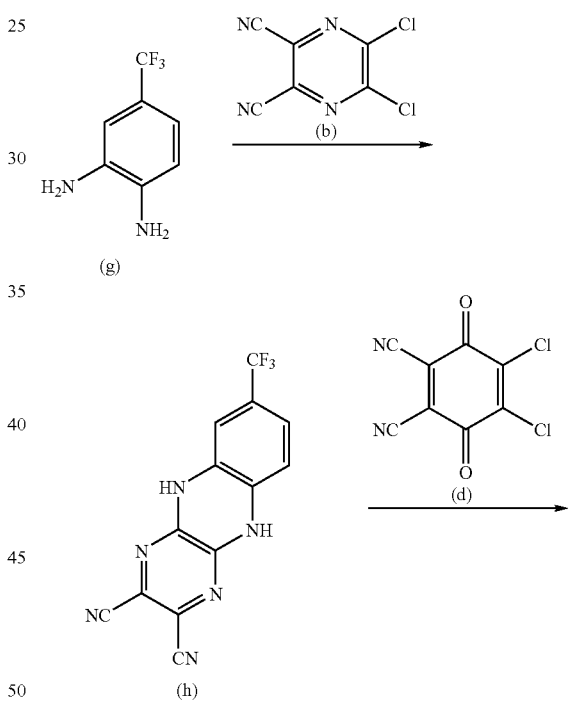

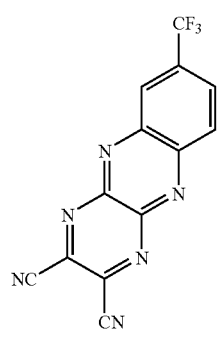

Compound (3)

Example 4

Synthesis of Compound (4)

15.6 g of 4-bromo-1,2-diaminobenzene (I), 25 g of 3,5-bis(trifluoromethyl)phenylboronic acid (O), 2.88 g of tetrakis(triphenylphosphine)palladium (K), and 26.5 g of sodium carbonate were dissolved in 125 ml of water to obtain an aqueous solution (L). The aqueous solution (L) and 150 ml of DME were introduced into a flask under an Ar atmosphere, and reacted under heat reflux for 8 hours. The reaction product was cooled down to room temperature, extracted with ethyl acetate, and then washed with water. Subsequently, the organic phase was dried over anhydrous magnesium sulfate, and the solvent was distilled off. The resulting crude product was purified by silica gel-chromatography (eluent: a mixed solvent of ethyl acetate and methyl chloride) to obtain 23 g of a compound (M).

Subsequently, 33 g of the compound (M) and 22 g of 5,6-dichloro-2,3-dicyanopyrazine (b) were reacted in acetonitrile under heat reflux under a nitrogen atmosphere for 8 hours. The reaction fluid was filtered, and the residue was washed with 50 ml of $CH_2Cl_2$ and with a saturated aqueous solution of $NaHCO_3$ to obtain 13.1 g of a compound (N).

Thereafter, 13 g of the compound (N) and 7.3 g of DDQ (d) were reacted in 450 ml of THF at room temperature under a nitrogen atmosphere for 8 hours. The reaction fluid was filtered, and the resulting solids were washed with THF, ethyl acetate, and $CH_2Cl_2$ to obtain 7.9 g of a compound (4). The compound (4) was subjected to the mass spectrometry (direct injection MS) and found to have m/e=444, so that the compound (4) was identified as the intended product. The product was purified by the sublimation purification.

The reduction potential of the purified compound (4) was measured in the same manner as that for Example 1, and thereby found to be −0.35 V (vs $Fc^+/Fc$).

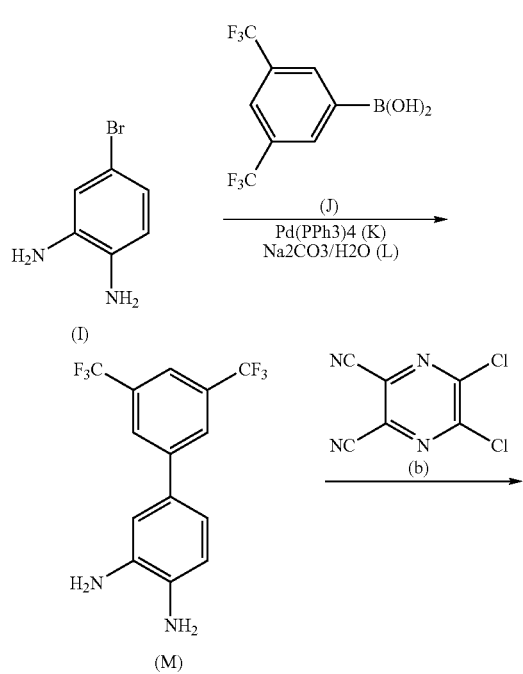

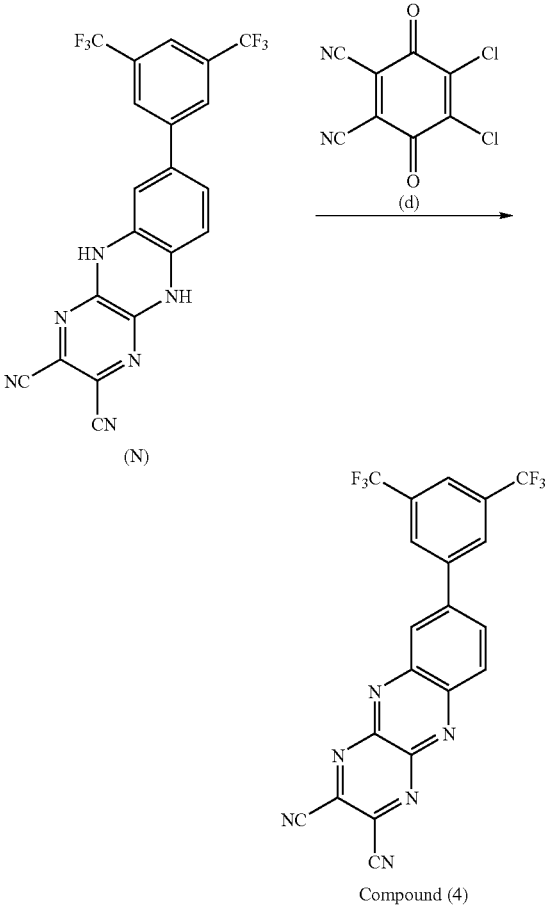

Compound (4)

Example 5

Synthesis of Compound (A-2)

Except for using 11 g of 5-fluoroacenaphthenequinone (o) in place of 10 g of acenaphthenequinone (e) used in Example 2, the same procedures for synthesis as those for Example 2 were carried out. Then, the product was subjected to the mass spectrometry (FDMS) and found to have m/e=324, so that the compound was identified as the intended product. The product was purified by the sublimation purification. The reduction potential of the resulting compound was measured in the same manner as that for Example 1, and thereby found to be −0.43 V (vs $Fc^+/Fc$).

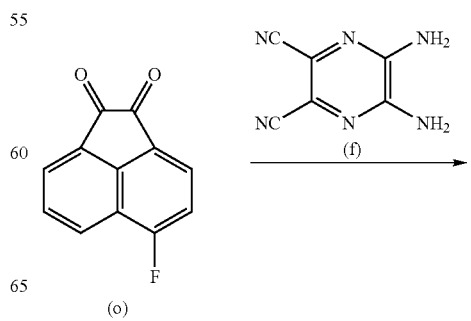

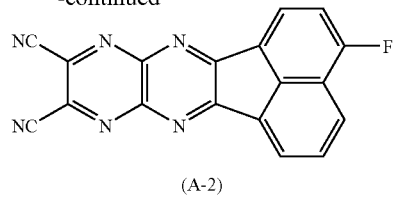

(A-2)

Example 6

Synthesis of Compound (A 10)

Except for using 12.5 g of aceanthrenequinone (p) in place of 10 g of acenaphthenequinone (e) used in Example 2, the same procedures for synthesis as those for Example 2 were carried out. Then, the product was subjected to the mass spectrometry (FDMS) and found to have m/e=356, so that the product was identified as the intended product. The reduction potential of the product was purified by the sublimation purification. The reduction potential of the resulting compound was measured in the same manner as that for Example 1, and thereby found to be −0.43 V (vs Fc$^+$/Fc).

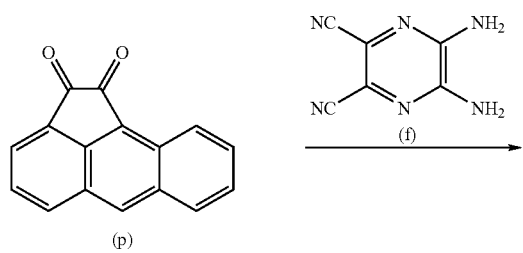

(A-10)

Example 7

Synthesis of Compound (A-21)

5.0 g of cyclopenta[fg]acenaphthylene-1,2,5,6-tetraone (q) and 7.0 g of 5,6-diamino-2,3-dicyanopyrazine (f) were reacted in 250 ml of pyridine under heat reflux for 18 hours. The reaction fluid was filtered at room temperature, and the resulting solid phase was washed with acetonitrile. The resulting solids were dried at 60° C. under reduced pressure for 8 hours to obtain 11 g of a compound (A-21). The compound (A-21) was subjected to the mass spectrometry (FDMS) and found to have m/e=484, so that the compound (A-21) was identified as the intended product. The product was purified by the sublimation purification. The reduction potential of the purified compound was measured in the same manner as that for Example 1, and thereby found to be −0.26 V (vs Fc$^+$/Fc).

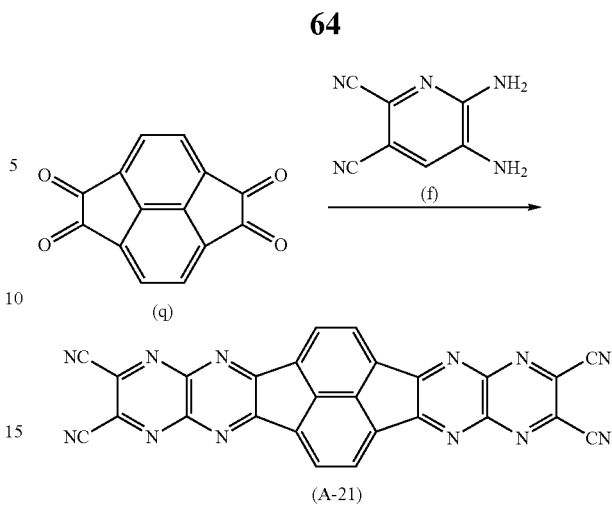

(A-21)

Example 8

Synthesis of Compound (A-26)

Except for using 6.0 g of a tetraone compound (r) described below in place of 5.0 g of cyclopenta[fg]acenaphthylene-1,2,5,6-tetraone used in Example 7, the same procedures for synthesis as those for Example 7 were carried out. Then, the product was subjected to the mass spectrometry (FDMS) and found to have m/e=534, so that the product was identified as the intended product. The product was purified by the sublimation purification. The reduction potential of the purified compound was measured as in the same manner as that for Example 1, and thereby found to be −0.27 V (vs Fc$^+$/Fc).

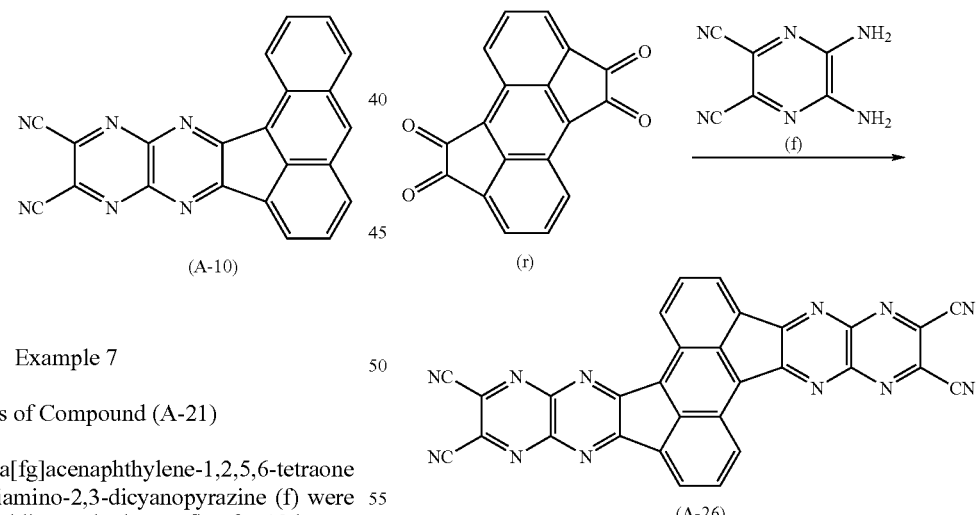

(A-26)

Example 9

Preparation of Organic EL Device Using Compound of Present Invention for the Hole Injecting Layer A transparent electrode made of indium tin oxide with a thickness of 120 nm was formed on a glass substrate having a size of 25 mm×75 mm×0.7 mm. The glass substrate was ultrasonically washed in isopropyl alcohol for 5 minutes and then washed with UV ozone for 30 minutes. Thereafter, the substrate was placed in a vacuum deposition apparatus.

The compound (I) was deposited in a thickness of 10 nm as a hole injecting layer on the substrate, and then, N—N'-bis[4'-{N-(naphthyl-1-yl)-N-phenyl}aminobiphenyl-4-yl]-N-phenylamine was deposited thereon in a thickness of 20 nm as a hole transporting layer.

Moreover, on the hole transporting layer, a film of a compound EM1 represented by the following general formula in a thickness of 40 nm, and a film of a styrylamine derivative S1 represented by the following general formula in a thickness ratio of 40:2 were formed to form a blue emitting layer.

A film of tris(8-hydroxyquinolinato)aluminum was formed by deposition in a thickness of 20 nm as an electron transporting layer on the blue emitting layer. After that, a film of LiF was formed in a thickness of 1 nm on the electron transporting layer. A metal Al was deposited in a thickness of 150 nm on the LiF film so as to be formed into a metal cathode. As a result, the organic EL emitting device was formed.

Compound (1)

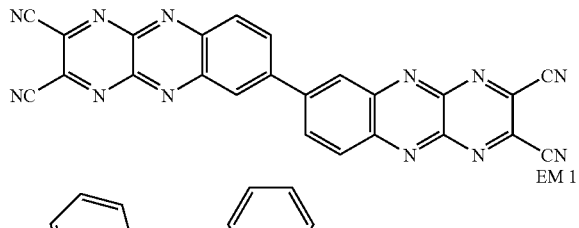

EM 1

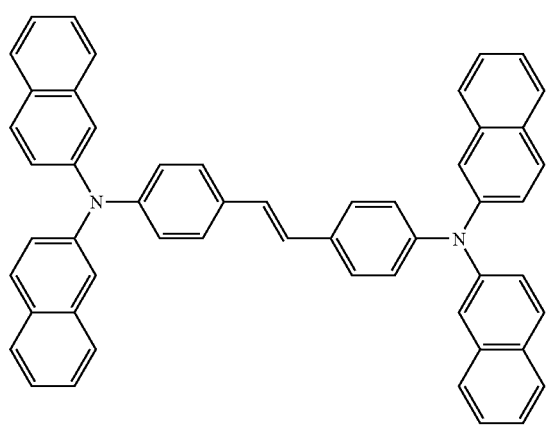

S 1

Example 10

Preparation of Organic EL Device Using Compound of Present Invention for Hole Injecting Layer A transparent electrode made of indium tin oxide with a thickness of 120 nm was formed on a glass substrate having a size of 25 mm×75 mm×0.7 mm. The glass substrate was ultrasonically washed in isopropyl alcohol for 5 minutes and then washed with UV ozone for 30 minutes. Thereafter, the substrate was placed in a vacuum deposition apparatus.

On the substrate, a 10 nm thickness film of the compound (I) synthesized in advance and N',N"-bis[4-(diphenylamino)phenyl]-N',N"-diphenylbiphenyl-4,4'-diamine (hereinafter referred to as compound (B)) was formed with a ratio of 2:98. This mixed film was designed to function as a hole injecting layer. N,N'-bis[4'-{N-(naphthyl-1-yl)-N-phenyl}aminobiphenyl-4-yl]-N-phenylamine was deposited on the hole injecting layer in a thickness of 20 nm as a hole transporting layer.

Moreover, on the hole transporting layer, a 40 nm thickness film of the compound EM1 and styrylamine derivative S1 was formed with a thickness ratio of 40:2 to form a blue emitting layer.

On this film, a film of tris(8-hydroxyquinolinato)aluminum was formed by deposition in a thickness of 20 nm as an electron transporting layer. After that, a film of LiF was formed in a thickness of 1 nm on the electron transporting layer. A metal Al was deposited in a thickness of 150 nm on the LiF film so as to form a metal cathode. As a result, the organic EL emitting device was formed.

Compound (B)

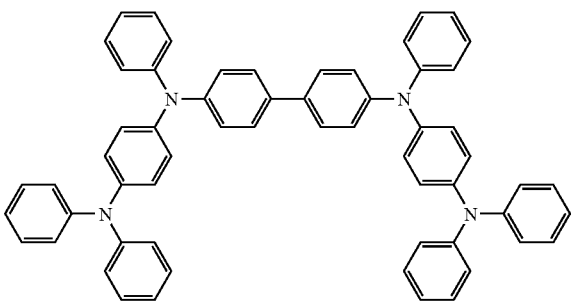

Example 11

Preparation of Organic EL Device Using Compound of Present Invention for Hole Injecting Layer A transparent electrode made of indium tin oxide with a thickness of 120 nm was formed on a glass substrate having a size of 25 mm×75 mm×0.7 mm. The glass substrate was ultrasonically washed in isopropyl alcohol for 5 minutes and then washed with UV ozone for 30 minutes. Thereafter, the substrate was placed in a vacuum deposition apparatus.

The compound (A-1) was deposited in a thickness of 10 nm as a hole injecting layer on the substrate, and then, N—N'-bis[4'-{N-(naphthyl-1-yl)-N-phenyl}aminobiphenyl-4-yl]-N-phenylamine was deposited thereon in a thickness of 20 nm as a hole transporting layer.

Moreover, on the hole transporting layer, a 40 nm thickness film of the compound EM1 and styrylamine derivative S1 was formed with a thickness ratio of 40:2 to form a blue emitting layer.

On this film, a film of tris(8-hydroxyquinolinato)aluminum was formed by deposition in a thickness of 20 nm as an electron transporting layer. After that, a film of LiF was formed in a thickness of 1 nm on the electron transporting layer. A metal Al was deposited in a thickness of 150 nm on the LiF film so as to form a metal cathode. As a result, the organic EL emitting device was formed.

Example 12

Preparation of Organic EL Device Using Compound of Present Invention for Hole Injecting Layer A transparent electrode made of indium tin oxide with a thickness of 120 nm was formed on a glass substrate having a size of 25 mm×75 mm×0.7 mm. The glass substrate was ultrasonically washed in isopropyl alcohol for 5 minutes and then washed with UV ozone for 30 minutes. Thereafter, the substrate was placed in a vacuum deposition apparatus.

On the substrate, a 10 nm thickness film of the compound (A-2) and the compound (B) both synthesized in advance was formed with a ratio of 2:98. This mixed film was designed to function as a hole injecting layer. N,N'-bis[4'-{N-(naphthyl-1-yl)-N-phenyl}aminobiphenyl-4-yl]-N-phenylamine was deposited on the hole injecting layer in a thickness of 20 nm as a hole transporting layer.

Moreover, on the hole transporting layer, a 40 nm thickness film of the compound EM1 and styrylamine derivative S1 was formed with a thickness ratio of 40:2 to form a blue emitting layer.

On this film, a film of tris(8-hydroxyquinolinato)aluminum was formed by deposition in a thickness of 20 nm as an electron transporting layer. After that, a film of LiF was formed in a thickness of 1 nm on the electron transporting layer. A metal Al was deposited in a thickness of 150 nm on the LiF film so as to form a metal cathode. As a result, the organic EL emitting device was formed.

Example 13

Preparation of Organic EL Device Using Compound of Present Invention for Hole Injecting Layer Except for using the compound (A-21) in place of the compound (A-1) for the hole injecting layer, the organic EL emitting device was prepared in the same manner as that for Example 11.

Comparative Example 1

Except for using the following compound (A) described in Japanese Patent No. 3614405 in place of the compound (I), the organic EL device was prepared in the same manner as that for Example 9.

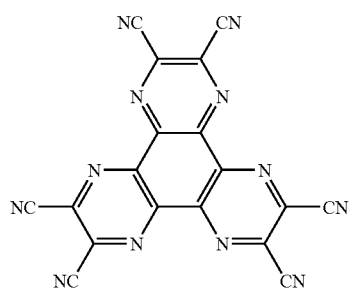

Compound (A)

Comparative Example 2

Except for using the compound (B) in place of the compound (I), the organic EL device was prepared in the same manner as that for Example 9.

(Evaluation of Organic EL Devices)

Each of the organic EL devices obtained in Examples 9 to 13 as well as Comparative Examples 1 and 2 was measured in terms of the voltage for obtaining a current density of 10 mA/cm$^2$, and the half life of luminance from an initial luminance of 1000 nits at room temperature with DC constant current driving. Moreover, the leakage current of each device was measured by applying a voltage of −5 V to the device. The results of measurements are shown in Table 1.

TABLE 1

| | Compound for Hole Injecting Layer | Voltage @ 10 mA/cm$^2$ (V) | Half-life (hr) | Leakage Current @ −5 V (μA) |
| --- | --- | --- | --- | --- |
| Example 9 | Compound (1) | 5.4 | | −0.0045 |
| Example 10 | Compound (1)/ Compound (B) | 5.5 | | −0.0028 |
| Example 11 | Compound (A-1) | 5.3 | 7000 | −0.0056 |
| Example 12 | Compound (A-2)/ Compound (B) | 5.5 | 7200 | −0.0028 |
| Example 13 | Compound (A-21) | 5.1 | 7200 | −0.0075 |
| Comparative Example 1 | Compound (A) | 5.3 | 6900 | −0.84 |
| Comparative Example 2 | Compound (B) | 6.4 | 6800 | −0.0019 |

As can be seen from the results shown in Table 1, using the compound according to the present invention for the hole injecting layer makes it possible to prepare a device having a low driving voltage, a long lifetime, and a small leakage current.

As described above in detail, the organic EL device using the compound according to the present invention has a low driving voltage, a long lifetime, and a small leakage current. For this reason, the compound according to the present invention can be used as a material for organic EL devices of various colors including a blue color, can be employed in the fields of various display devices, displays, backlights, light sources of lighting apparatuses, signals, advertising displays, interior, and the like, and in particular is suitable for display devices of color displays.

What is claimed is:

1. A compound represented by one of the following general formulas (2) to (4):

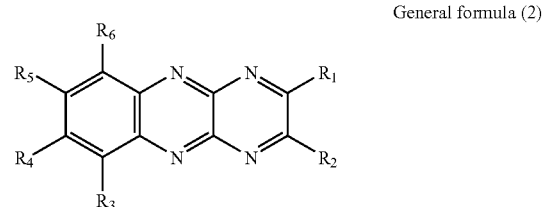

General formula (2)

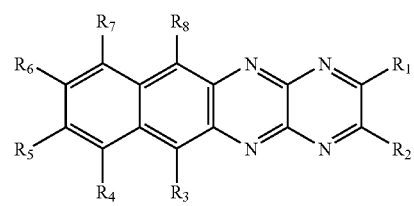

General formula (3)

General formula (4)

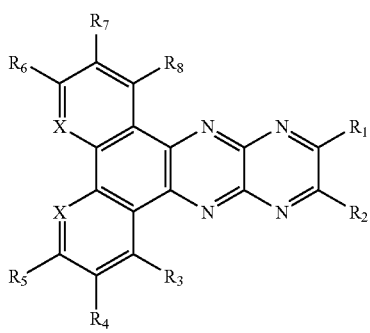

wherein $R_1$ and $R_2$ are a cyano group; and $R_3$ to $R_8$ are each selected from the group consisting of a hydrogen atom, substituted or unsubstituted alkyl groups, substituted or unsubstituted aryl groups, substituted or unsubstituted heterocyclic rings, halogen atoms, a cyano group, a nitro group, ester groups, amide groups, alkoxy groups, substituted or unsubstituted phenoxy groups, and an amino group, and may be the same or different; those of $R_3$ to $R_8$, which are adjacent to one another, may be linked together to form a ring structure, provided that at least one of $R_3$ to $R_8$ is selected from the group consisting of substituted alkyl groups, substituted aryl groups, substituted or unsubstituted heterocyclic rings, halogen atoms, a cyano group, a nitro group, ester groups, amide groups, substituted or unsubstituted phenoxy groups, and an amino group and at least one of $R_3$ to $R_8$ represents a fluorine-containing substituent; and X represents N or CH.

2. A material for organic electroluminescence devices, comprising the compound according to claim 1.

3. A hole injecting material or a hole transporting material for an organic electroluminescence device, comprising the compound according to claim 1.

4. An organic electroluminescence device having at least a pair of electrodes and an organic emitting layer sandwiched by the electrodes, the device comprising the compound according to claim 1.

5. The organic electroluminescence device according to claim 4, further comprising a hole injecting layer or a hole transporting layer, wherein the hole injecting layer or the hole transporting layer comprises the compound.

6. An apparatus comprising the organic electroluminescence device according to claim 4.

* * * * *